US008577240B2

(12) United States Patent
Horii et al.

(10) Patent No.: US 8,577,240 B2
(45) Date of Patent: Nov. 5, 2013

(54) SENSOR MEMBER AND IMAGE FORMING APPARATUS

(75) Inventors: Kiyohito Horii, Kanagawa (JP); Takeshi Okoshi, Kanagawa (JP); Masaaki Tokunaga, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 156 days.

(21) Appl. No.: 13/112,808

(22) Filed: May 20, 2011

(65) Prior Publication Data

US 2012/0114360 A1    May 10, 2012

(30) Foreign Application Priority Data

Nov. 10, 2010  (JP) ................................. 2010-252370

(51) Int. Cl.
*G03G 15/00*    (2006.01)
(52) U.S. Cl.
USPC ............................................ 399/74; 399/107
(58) Field of Classification Search
USPC .................................................... 399/74, 107
See application file for complete search history.

(56) References Cited

FOREIGN PATENT DOCUMENTS

| JP | 4-349480 A | 3/1992 |
| JP | 5-142906 A | 6/1993 |
| JP | 7-181796 A | 7/1995 |
| JP | 11065397 A * | 3/1999 |
| JP | 2001-66874 A | 3/2001 |
| JP | 2008-185848 A | 8/2008 |

OTHER PUBLICATIONS

Kouchi (JP 11-065397 A), Mar. 1999, JPO Machine Translation.*

* cited by examiner

*Primary Examiner* — David Gray
*Assistant Examiner* — Erika J Villaluna
(74) *Attorney, Agent, or Firm* — Sughrue Mion, PLLC

(57) ABSTRACT

An image forming apparatus includes a sensor member having first and second ends opposite to each other in a longitudinal direction of the sensor member and supported by support structures consisting of the first and second ends, and first and second support portions supporting the first and second ends; a first support structure including a first protruding portion fitted on a first recess portion supporting the first protruding portion; and a second support structure including a second protruding portion fitted on a second recess portion supporting the second protruding portion. The second protruding portion has first and second cylinder portions extending in a longitudinal direction of the second protruding portion. The second recess portion has an insertion portion allowing the second protruding portion to be inserted, a pass portion allowing the first cylinder portion to pass therethrough, and a positioning portion fitted on the second cylinder portion.

18 Claims, 12 Drawing Sheets

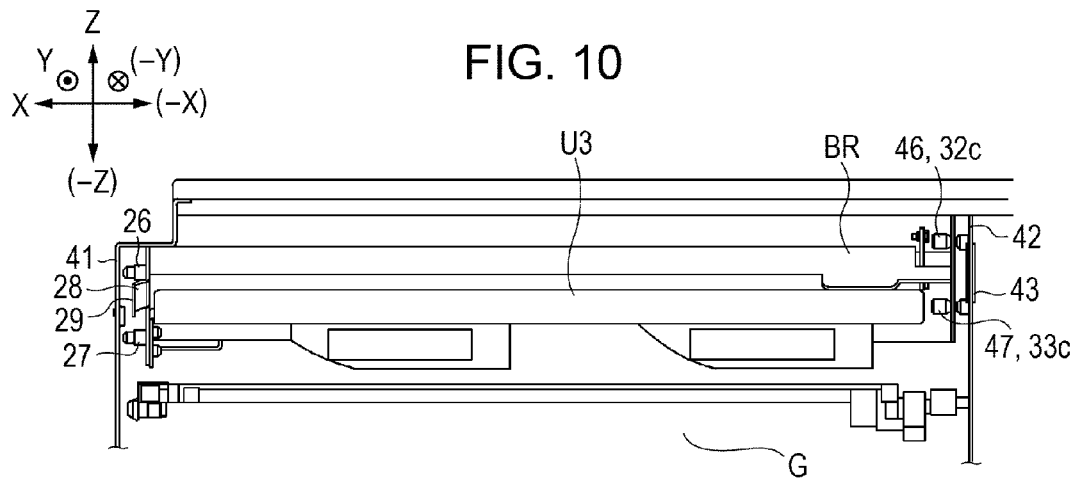
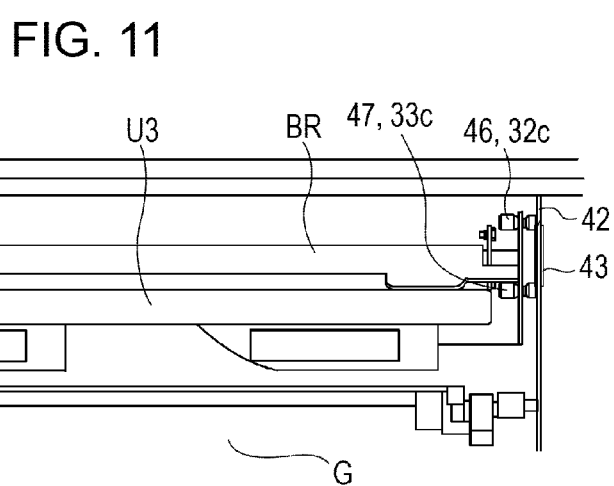
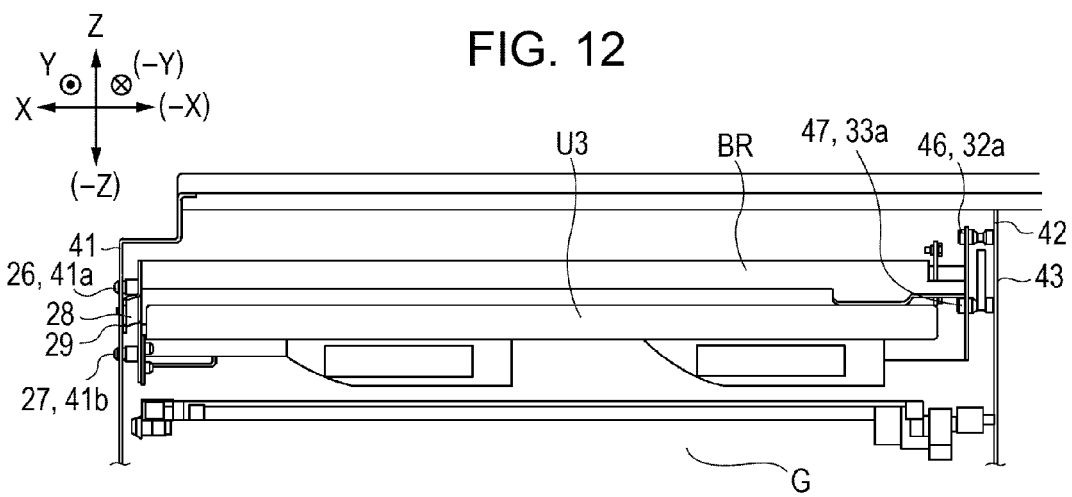

SENSOR MEMBER AND IMAGE FORMING APPARATUS

CROSS-REFERENCE TO RELATED APPLICATIONS

This application is based on and claims priority under 35 USC 119 from Japanese Patent Application No. 2010-252370 filed Nov. 10, 2010.

BACKGROUND

The present invention relates to a sensor member that detects a density of a developer or a toner, and also relates to an image forming apparatus.

SUMMARY

There is provided an image forming apparatus according to an aspect of the present invention. The image forming apparatus includes a sensor member, a first support structure, and a second support structure. The sensor member is mounted in the image forming apparatus, detects a developer, has a first end and a second end opposite to each other in a longitudinal direction of the sensor member, and is supported by support structures of the image forming apparatus, the support structures consisting of the first end, the second end, a first support portion of the image forming apparatus, and a second support portion of the image forming apparatus, the first support portion supporting the first end, the second support portion supporting the second end. The first support structure includes a first protruding portion that is fitted on a first recess portion, the first recess portion supporting the first protruding portion movably in the longitudinal direction of the sensor member. The second support structure supports the second end of the sensor member. The second support structure includes a second protruding portion that is fitted on a second recess portion, the second recess portion supporting the second protruding portion movably in a direction defined by connecting the first end and the second end. The second protruding portion has a first cylinder portion that extends in a longitudinal direction of the second protruding portion, and a second cylinder portion that is arranged at an end side of the second protruding portion next to the first cylinder portion, the second cylinder portion having a larger external shape than an external shape of the first cylinder portion and extending in the longitudinal direction of the second protruding portion. The second recess portion has an insertion portion that allows the second protruding portion to be inserted, and that is larger than the external shape of the second cylinder portion; a pass portion that is connected with the insertion portion, that is larger than the external shape of the first cylinder portion and smaller than the external shape of the second cylinder portion, and that allows the first cylinder portion to pass therethrough; and a positioning portion that is connected with the pass portion, and that has a shape corresponding to the external shape of the second cylinder portion, the positioning portion being fitted on the second cylinder portion and supporting the second cylinder portion such that the sensor member is positioned.

BRIEF DESCRIPTION OF THE DRAWINGS

Exemplary embodiment(s) of the present invention will be described in detail based on the following figures, wherein:

FIG. 10 is an enlarged explanatory view showing a specific portion in a sate in which the front side of the sensor bracket is moved from the state in FIG. 9 and the sensor bracket is arranged perpendicularly to the front and rear supports;

FIG. 11 is an explanatory view in a state in which the sensor bracket is moved upward from the state in FIG. 10 and hence the rear studs pass through coupling holes and penetrate through upper through holes;

FIG. 12 is an explanatory view of a state in which the sensor bracket is moved forward from the state in FIG. 11 and hence the studs at both front and rear ends respectively penetrate through the through holes, are fitted to the through holes, and are positioned;

DETAILED DESCRIPTION

Figure 1:
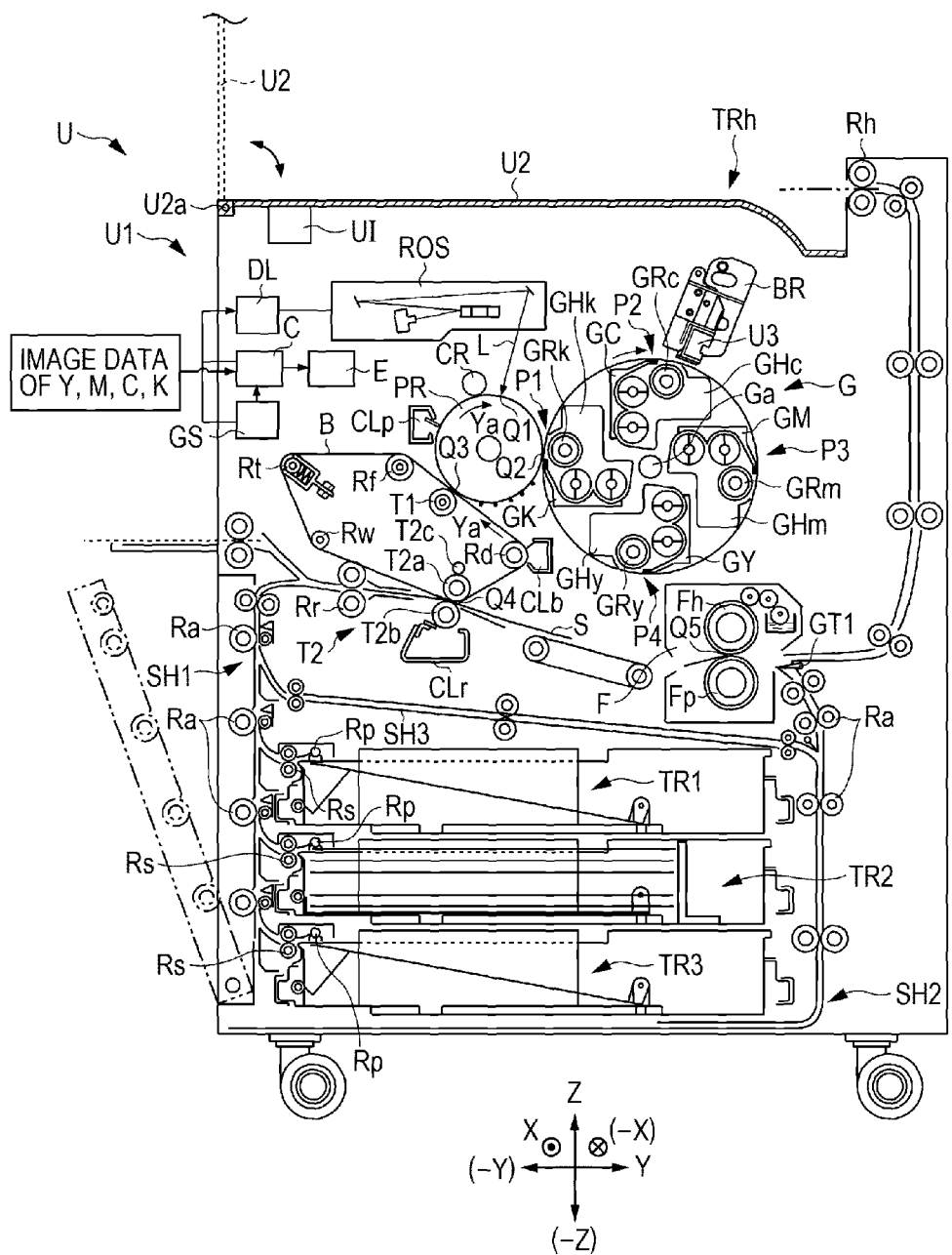
FIG. 1 is a general explanatory view of an image forming apparatus according to a first exemplary embodiment.

A specific example of an exemplary embodiment of the present invention (hereinafter, referred to as exemplary embodiment) will be described next with reference to the accompanying drawings. However, the present invention is not limited to the exemplary embodiment described below.

For easier understanding of the description given below, in the drawings, it is assumed that a front-rear direction is an X-axis direction, a left-right direction is a Y-axis direction, and an up-down direction is a Z-axis direction; and directions or sides indicated by arrows X, −X, Y, −Y, Z, and −Z are respectively forward, rearward, rightward, leftward, upward, and downward, or front side, rear side, right side, left side, upper side, and lower side.

Also, in the drawings, it is assumed that a circle "O" with a dot "•" therein represents an arrow directed from the back side to the front side of a sheet, and a circle "O" with a cross "X" therein represents an arrow directed from the front side to the back side of the sheet.

In the description with reference to the drawings, illustration of members other than members required for the description is occasionally omitted for the convenience of understanding.

First Exemplary Embodiment

FIG. 1 is a general explanatory view of an image forming apparatus according to a first exemplary embodiment.

In FIG. 1, a printer U, which is an example of an image forming apparatus according to the first exemplary embodiment, includes a printer body U1, which is an example of an image forming apparatus body, and a sheet output tray TRh, which is an example of a body output portion, provided on an upper surface of the printer body U1. An open/close cover U2 is supported at the sheet output tray TRh of the first exemplary embodiment such that the open/close cover U2 is rotatable around a rotation center U2a located at a right end. The open/close cover U2 is an example of an open/close member that is opened and closed for replacement of a replaceable member provided in the apparatus.

Sheet feed trays TR1 to TR3, each of which is an example of a sheet feed container that houses a recording sheet S, which is an example of a medium on which an image is recorded, are housed in a lower portion of the printer body U1.

Also, the printer body U1 of the first exemplary embodiment includes an operation unit UI, which is operated by an input of a user, and a controller C. The printer body U1 also includes a laser drive circuit DL, which is an example of a drive circuit for a latent-image forming device, an image processor GS, a power supply circuit E, etc., controlled by the controller C. The controller C of the first exemplary embodiment includes an input/output interface (I/O), which is an example of an input/output signal adjuster that performs input/output of a signal to/from an external device and adjustment etc. of an input/output signal level, a read-only memory (ROM) that stores programs and data etc. for executing required processing, a random-access memory (RAM) that temporarily stores required data, a central processing unit (CPU) that performs processing in accordance with the programs stored in the ROM, and a computer, which is an example of a calculator including a clock oscillator etc. Various functions may be provided by executing the programs stored in the ROM.

The image processor GS converts image information, i.e., image data input from an external information processing device or the like into image data for writing, temporarily stores the image data, and outputs the image data as image data for latent-image formation at a predetermined time, i.e., timing to the laser drive circuit DL. The laser drive circuit DL outputs a laser drive signal to a latent-image forming device ROS in accordance with the input image data. The latent-image forming device ROS emits image forming light for image writing, i.e., a laser beam L in accordance with the laser drive signal. The controller C controls operations of the operation unit UI, the image processor GS, and the laser drive circuit DL, as well as the power supply circuit E etc. that applies a voltage to development rollers GRy to GRk and transfer rollers T1 and T2b, which will be described later.

An image holding member PR that is configured of a photoconductor drum rotates in an arrow Ya direction. The surface of the image holding member PR is uniformly electrically charged by a charging roller CR, which is an example of a charging member, and then is exposed with light by scanning with the laser beam L of the latent-image forming device ROS at a latent-image forming position Q1. Thus, an electrostatic latent image is formed. When a full-color image is formed, electrostatic latent images corresponding to images of four colors including yellow (Y), magenta (M), C (cyan), and black (K) are successively formed. When a monochrome image is formed, only an electrostatic latent image corresponding to an image of black (K) is formed.

The surface of the image holding member PR with the electrostatic latent images formed thereon rotationally moves, and successively passes through a development region Q2 and a first transfer region Q3.

A rotary developing device G that develops the electrostatic latent image in the development region Q2 includes developing units GY, GM, GC, and GK of four colors including yellow (Y), magenta (M), cyan (C), and black (K). The developing units GY, GM, GC, and GK successively rotationally move to the development region Q2 by rotation of a rotation shaft Ga. In particular, the developing units GY to GK are arranged such that phases thereof are shifted by 90° around the rotation shaft Ga. During a color-image recording operation, the developing units GY to GK successively rotationally move to and stop at a development position P1, which is an example of a first stop position at which the developing device G faces the image holding member PR.

An initial position, i.e., a home position of the developing device G of the first exemplary embodiment is set such that the black developing unit GK, which is frequently used, is stopped at the development position P1 as an example of a first stop position, at which the black developing unit GK faces the image holding member PR. Accordingly, when an image forming operation, i.e., a job for a monochrome image of black (K) is executed, the monochrome image is printed immediately. At the initial position, the developing units GC, GM, and GY are respectively stopped at a detection position P2, which is an example of a second stop position, a third stop position P3, and a fourth stop position P4 that are rotated counterclockwise by 90°, 180°, and 270° from the black developing unit GK.

The developing units GY to GK of the respective colors include development containers GHy, GHm, GHc, and GHk that house developers, and development rollers GRy, GRm, GRc, and GRk, each of which is an example of a developer holding member that transports a developer to the development region Q2. Accordingly, the electrostatic latent images on the image holding member PR that passes through the development region Q2 into toner images, each of which is an example of a visible image.

The developing units GY to GK have developing unit bodies that are supplied with developers, i.e., toners of respective colors from toner cartridges (not shown), each of which is an example of a developer supply container.

The first transfer region Q3 is a region where an intermediate transfer belt B, which is an example of an intermediate transfer member that rotationally moves in the arrow Ya direction, is pressed to the surface of the image holding member PR by a roller-like first transfer unit T1. The power source circuit E supplies a first transfer voltage to the first transfer unit T1. The first transfer voltage has a polarity opposite to a charging polarity of a toner for development, which is an example of a developer used in the developing device G.

The toner image developed on the surface of the image holding member PR is first transferred on the intermediate transfer belt B by the first transfer unit T1 in the first transfer region Q3. After the first transfer, an image holding member cleaner CLp, which is an example of an image holding member cleaner, cleans a residual toner on the surface of the image holding member PR.

The intermediate transfer belt B that rotationally moves in the arrow Ya direction is rotatably supported by a driving roller Rd, which is an example of a driving member, a tension roller Rt, which is an example of a tension generating member, a walking roller Rw, which is an example of an extension member, an idle roller Rf, which is an example of a support member, and a backup roller T2a, which is an example of an opposite member. A second transfer roller T2b, which is an example of a second transfer member, is arranged at a position at which the second transfer roller T2b faces the backup roller T2a with the intermediate transfer belt B arranged therebetween. The second transfer roller T2b may move toward and away from the backup roller T2a. A region where the second transfer roller T2b is pressed to the intermediate transfer belt B defines a second transfer region Q4. A roll cleaner CLr, which is an example of a second transfer member cleaner, cleans the second transfer roller T2b.

Also, a contact roller T2c, which is an example of a second transfer voltage supply member and made of conductive metal, contacts the backup roller T2a. The power supply circuit E supplies a second transfer voltage, which has the same polarity as the charging polarity of the toner, to the contact roller T2c. The rollers T2a to T2c define a second transfer unit T2.

When a full-color image is formed, a first-color electrostatic latent image is formed at the latent-image forming position Q1, and a first-color toner image is formed in the development region Q2. This toner image is electrostatically first transferred on the intermediate transfer belt B by the first transfer unit T1 when the toner image passes through the first transfer region Q3. Then, similarly, second-color, third-color, and fourth-color toner images are first transferred on the intermediate transfer belt B that carries the first-color toner image, in a manner successively superposed on each other. Finally, a full-color superposed toner image is formed on the intermediate transfer belt B.

When a monochrome image is formed, only a single developing unit is used, and a single-color toner image is first transferred on the intermediate transfer belt B.

The image holding member PR, the charging roller CR, the laser drive circuit LD, the latent-image forming device ROS, the developing device G, the first transfer unit T1, and the intermediate transfer belt B, etc., define a toner image forming device PR+CR+LD+ROS+G+T1+B, as an example of a visible image forming device.

A recording sheet S that is picked up from one of the sheet feed trays TR1 to TR3 at a predetermined timing is transported to the second transfer region Q4 at a timing corresponding to that the first transferred superposed toner image or the single-color toner image is moved to the second transfer region Q4.

In particular, recording sheets S in one of the trays TR1 to TR3 are picked up by a pickup roller Rp at a predetermined timing, the recording sheets S are separated one by one by a sheet separation roller Rs, the separated recording sheet S is transported through a sheet transport path SH1, which is an example of a medium transport path including multiple transport rollers Ra, and the transported recording sheet S is transported to a registration roller Rr.

The recording sheet S transported to the registration roller is transported to the second transfer region Q4 at a timing corresponding to that the first transferred superposed toner image or the single-color toner image is moved to the second transfer region Q4.

In the second transfer region Q4, the second transfer unit T2 electrostatically second transfer the toner image on the intermediate transfer belt B collectively onto the recording sheet S. A belt cleaner CLb, which is an example of an intermediate transfer member cleaner, removes a residual toner on the intermediate transfer belt B after the second transfer.

When the recording sheet S with the toner image second transferred thereon passes through a fixing region Q5, a fixing device F including a heat roller Fh, which is an example of a heat member, and a pressure roller Fp, which is an example of a pressure member, heats and fixes the toner image. Then, a sheet output roller Rh, which is an example of an output member, outputs the recording sheet S onto the sheet output tray TRh.

A switch gate GT1, which is an example of a switch member, is arranged downstream of the fixing device F. The switch gate GT1 selects a transport direction of the recording sheet S which has passed through the fixing device F, from a direction toward the sheet output Tray TRh and a direction toward a sheet reverse path SH2, which is an example of a medium reverse path and includes transport rollers Ra.

For duplex copying, a recording sheet S with a toner image transferred on a first side is reversed at the sheet reverse path SH2, passes through a sheet circulation path SH3, which is an example of a medium circulation path, and is transported to the second transfer region Q4 again. Then, a toner image is transferred on a second side of the recording sheet S.

Figure 2:
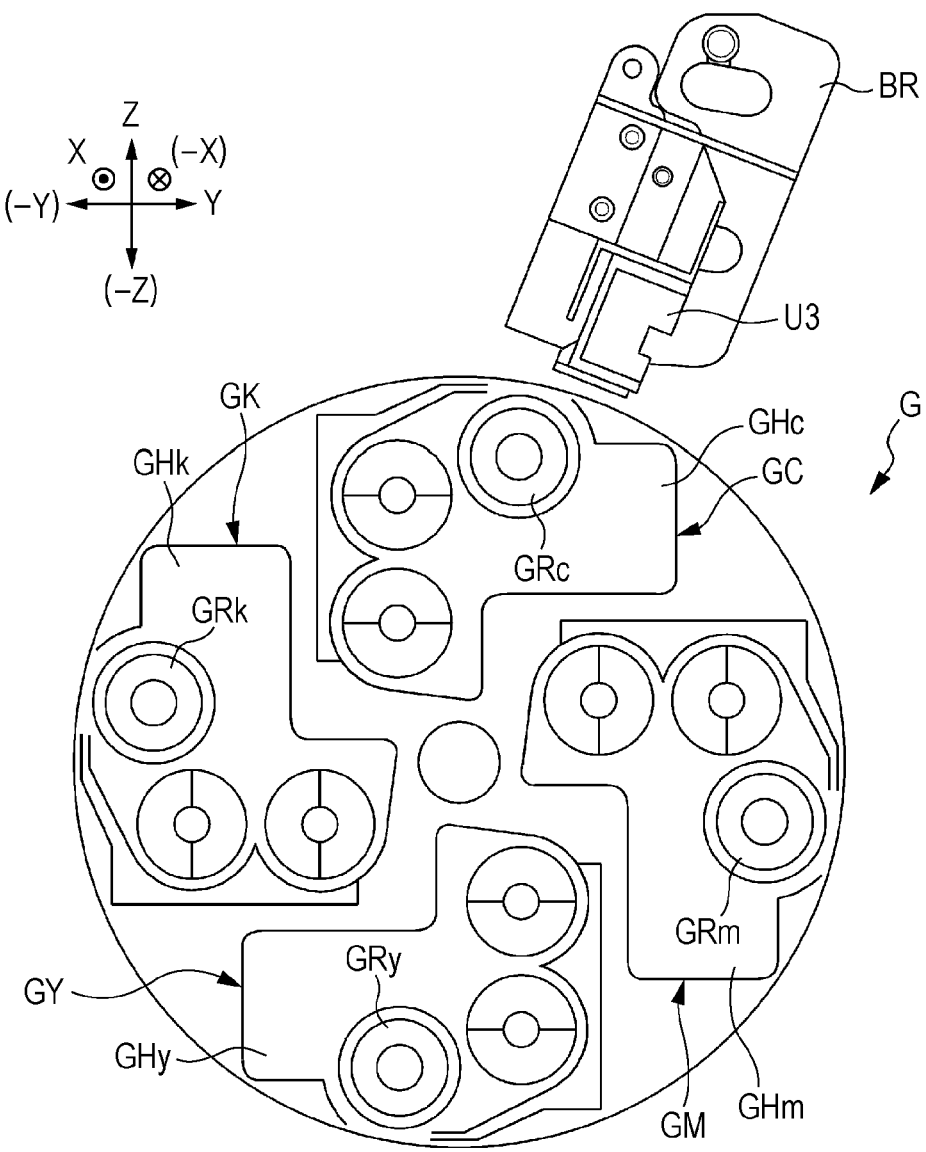
FIG. 2 is an enlarged explanatory view showing a specific portion of a developing device and a sensor unit according to the first exemplary embodiment.

Description for Attachment Mechanism Between Sensor Bracket BR and Front and Rear Supports 41 and 42 According to First Exemplary Embodiment FIG. 2 is an enlarged explanatory view showing a specific portion of a developing device and a sensor unit according to the first exemplary embodiment.

Figure 3A:
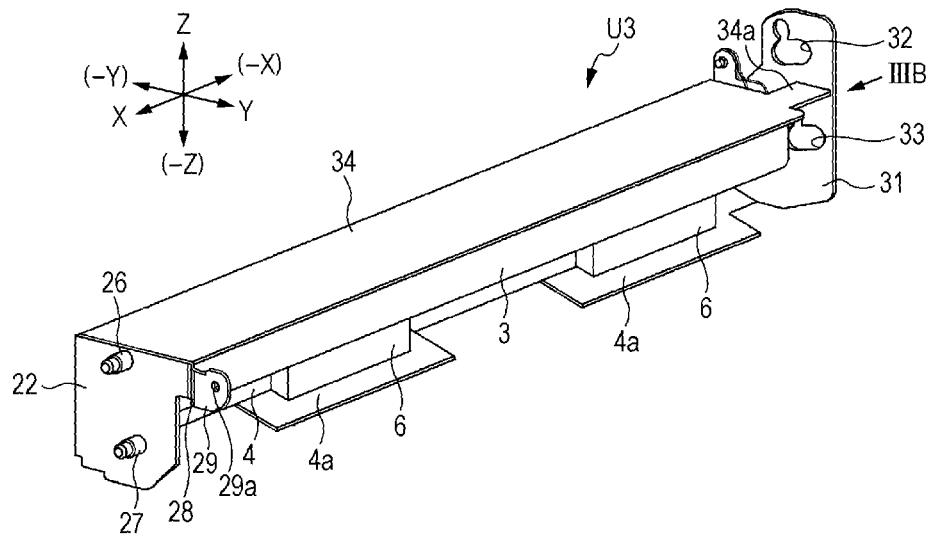
FIGS. 3A and 3B are enlarged explanatory views of the sensor unit and a sensor bracket according to the first exemplary embodiment, FIG. 3A being a perspective view of the sensor unit and the sensor bracket, FIG. 3B being a perspective view when viewed from arrow IIIB in FIG. 3A.
Figure 3B:
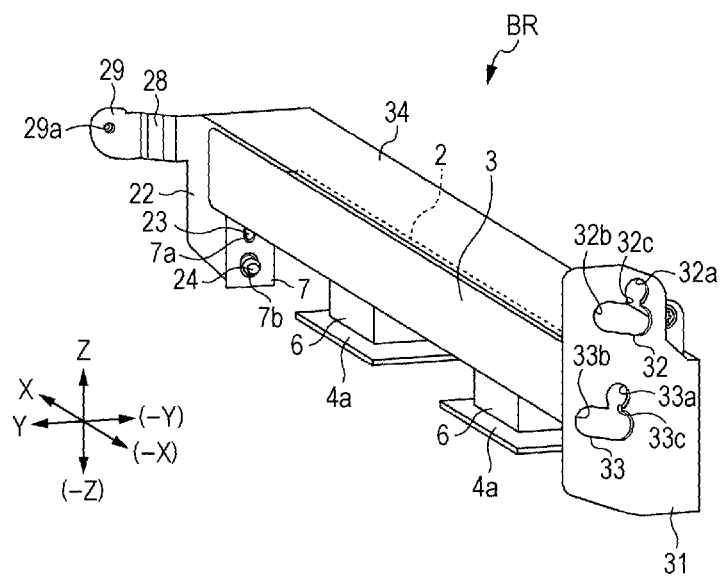

FIGS. 3A and 3B are enlarged explanatory views of the sensor unit and a sensor bracket according to the first exemplary embodiment, FIG. 3A being a perspective view of the sensor unit and the sensor bracket, FIG. 3B being a perspective view when viewed from arrow IIIB in FIG. 3A.

Figure 4A:
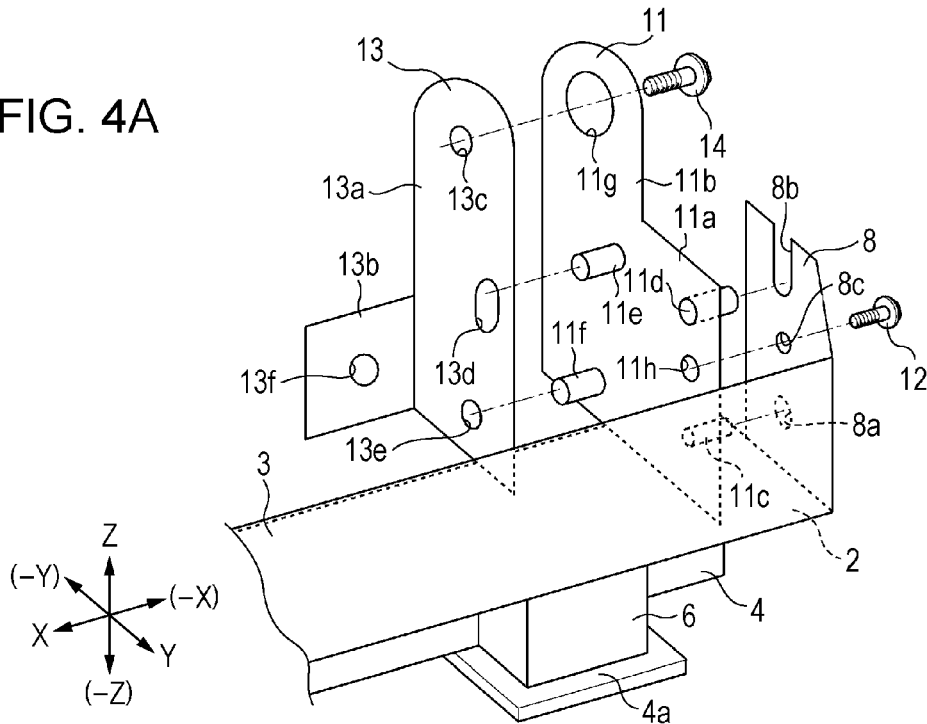
FIGS. 4A and 4B are explanatory views of a unit frame according to the first exemplary embodiment, FIG. 4A being an enlarged explanatory view showing a specific portion of the unit frame and first and second coupling plates, FIG. 4B being an enlarged explanatory view of a state in which the unit frame and the first and second coupling plates are coupled together.
Figure 4B:
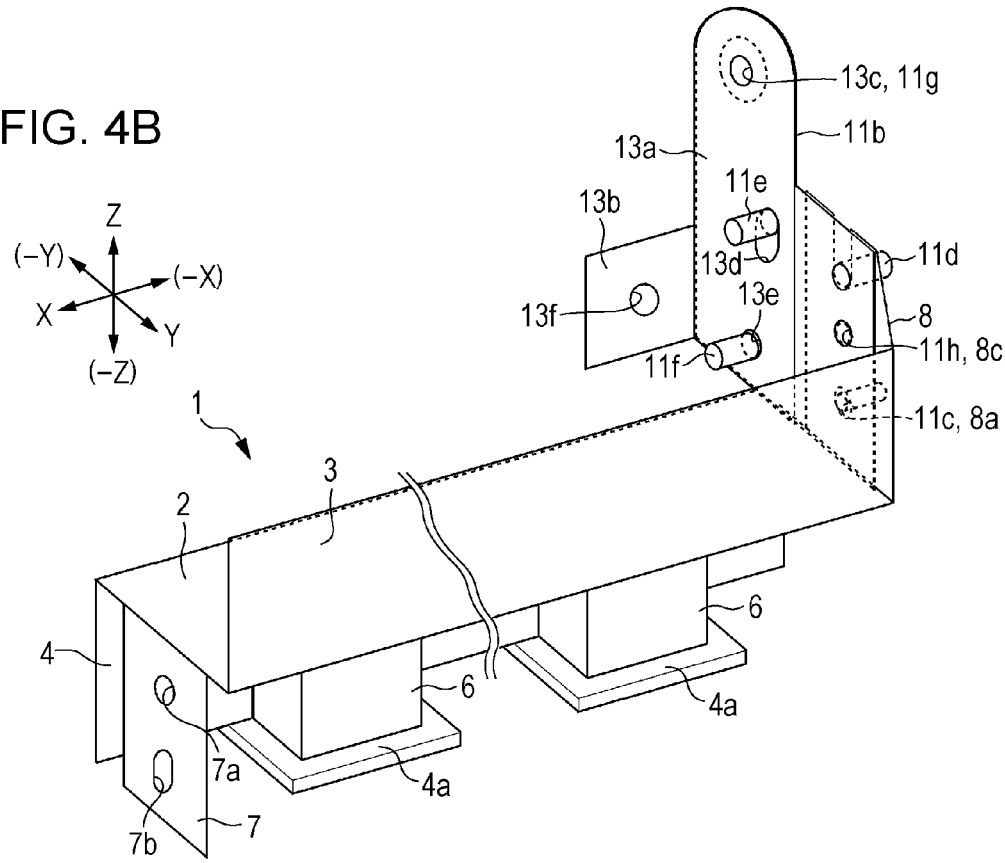

FIGS. 4A and 4B are explanatory views of a unit frame according to the first exemplary embodiment, FIG. 4A being an enlarged explanatory view showing a specific portion of the unit frame and first and second coupling plates, FIG. 4B being an enlarged explanatory view of a state in which the unit frame and first and second coupling plates are coupled together.

In FIGS. 1 and 2, a sensor unit U3, which is an example of a sensor member body, is arranged above the developing device G. In FIGS. 3A, 3B, 4A, and 4B, the sensor unit U3 includes a unit frame 1, which is an example of a sensor support, extending in the front-rear direction.

The unit frame 1 of the first exemplary embodiment includes a plate-like center plate 2, which is an example of a center plate portion, extending in the front-rear direction. A flat-plate-like upper right plate 3, which is an example of an upper right plate portion, extending upward is formed at a right end of the center plate 2. A flat-plate-like lower left plate 4, which is an example of a lower left surface, extending downward is formed at a left end of the center plate 2. A pair of flat-plate-like front and rear body-support plates 4a, each of which is an example of a body-support plate portion, extending rightward and arranged at an interval in the front-rear direction are supported at a lower end of the lower left plate 4. A pair of front and rear sensor bodies 6, each of which is an example of a sensor, are supported at the body-support plates 4a. The sensor bodies 6 of the first exemplary embodiment are arranged above the development rollers GRy to GRc of the developing units GY to GC to face the development rollers GRy to GRc when each of the developing units GY to GC rotates counterclockwise by 90° from the development position P1 and moves to the detection position P2. The sensor bodies 6 are configured of sensors that irradiate the development rollers GRy to GRc with detection light when each of the development rollers GRy to GRc moves to the detection position P2, receive reflection light of the detection light, and estimate densities of toners in the development containers GHy to GHc.

With the reflective sensors, it is difficult to accurately detect the density of the black (K) toner because the black toner absorbs the detection light. Hence, in the first exemplary embodiment, the sensors only detect the densities of the toners of the developing units GY to GC of Y, M, and C colors when each of the developing units GY to GC moves to the detection position P2.

In the first exemplary embodiment, when the developing units GY to GC of Y to C colors rotationally move from the detection position P2 to the development position P1, the developers of Y to C colors are respectively supplied from the toner cartridges to the developing units GY to GC in accordance with toner use amounts based on the number of pixels written by the latent-image forming device ROS and in accordance with the estimated toner densities. When the developing unit GK of K color rotationally moves to the development position P1, since the toner density is not detected, the developer of K color is supplied from the toner cartridge in accordance with the toner use amount.

Also, a flat-plate-like front positioned plate 7 extending downward is formed as an example of a front lower plate portion and an example of a front positioned plate portion, at a center portion in the left-right direction of a front end of the center plate 2. As shown in FIGS. 3B and 4B, an upper positioned hole 7a and a lower positioned long hole 7b are formed at a center portion of the front positioned plate 7. The lower positioned long hole 7b is arranged below the upper positioned hole 7a and extends in the up-down direction. Also, a flat-plate-like rear coupling plate 8 extending upward is formed as an example of a rear upper plate portion and an example of a rear coupling plate portion, at a rear end of the center plate 2. As shown in FIGS. 4A and 4B, a lower positioned hole 8a, an upper positioned long hole 8b, and a first coupling hole 8c are formed at a center portion in left part of the rear coupling plate 8. The upper positioned long hole 8b is arranged above the lower positioned hole 8a and is formed by cutting an upper portion of the rear coupling plate 8 to have a semicircular shape. The first coupling hole 8c is formed at a center portion in the up-down direction between the lower positioned hole 8a and the upper positioned long hole 8b.

Also, a flat-plate-like first coupling plate 11 is arranged as an example of a first coupling member, at the front side of the rear coupling plate 8. The first coupling plate 11 includes a flat-plate-like right coupling portion 11a that faces a left portion of the rear coupling plate 8, and a left coupling portion 11b that is arranged at the left side of the right coupling portion 11a and extends upward by a larger length than a length of the right coupling portion 11a.

In FIGS. 4A and 4B, the right coupling portion 11a has a lower positioning boss 11c, which is an example of a lower positioning protrusion, at a position corresponding to the lower positioned hole 8a; and an upper positioning boss 11d, which is an example of an upper positioning protrusion, arranged above the lower positioning boss 11c, at a position corresponding to the upper positioned long hole 8b. Also, a first coupling screw hole 11h is formed at a center portion in the up-down direction between the lower positioning boss 11c and the upper positioning boss 11d, at a position corresponding to the first coupling hole 8c.

In the first exemplary embodiment, the rear coupling plate 8 is coupled with the first coupling plate 11, by coupling the first coupling hole 8c and the first coupling screw hole 11h together by using a first screw 12, which penetrates through these holes from the rear side, while the lower positioning boss 11c and the upper positioning boss lid are fitted to the lower positioned hole 8a and the upper positioned long hole 8b.

As shown in FIGS. 4A and 4B, an upper positioning pin 11e, which is an example of an upper positioning protrusion, and a lower positioning pin 11f, which is an example of a lower positioning protrusion, are formed in a right portion of the left coupling portion 11b. The lower positioning pin 11f is arranged below the upper positioning pin 11e. Also, a second coupling hole 11g is formed in an upper end portion of the left coupling portion 11b.

Also, a second coupling plate 13 is arranged as an example of a second coupling member, at the front side of the first coupling plate 11. The second coupling plate 13 includes a flat-plate-like rear coupling portion 13a facing the left coupling portion 11b, and a flat-plate-like front coupling portion 13b formed by being bent forward from a left end of the rear coupling portion 13a and having a lower height in the up-down direction than a height of the rear coupling portion 13a.

In FIGS. 4A and 4B, an upper positioned long hole 13d and a lower positioned hole 13e are formed in a right portion of the rear coupling portion 13a. The upper positioned long hole 13d extends in the up-down direction and corresponds to the upper positioning pin 11e. The lower positioned hole 13e is arranged below the upper positioned long hole 13d and corresponds to the lower positioning pin 11f. Also, a second screw hole 13c is formed in an upper end portion of the rear coupling portion 13a, at a position corresponding to the second coupling hole 11g. In the first exemplary embodiment, the first coupling plate 11 and the second coupling plate 13 are coupled together by coupling the second screw hole 13c and the second coupling hole 11g together by using a second screw 14, which penetrates through these holes from the rear side, while the upper positioning pin 11e and the lower positioning pin 11f are fitted to the upper positioned long hole 13d and the lower positioned hole 13e.

Also, a third coupling hole 13f is formed in a center portion of the front coupling portion 13b, for coupling with a bracket BR.

The upper positioned hole 7a, the lower positioned long hole 7b, and the third coupling hole 13f define a unit supported portion 7a+7b+13f of the first exemplary embodiment.

Figure 5A:
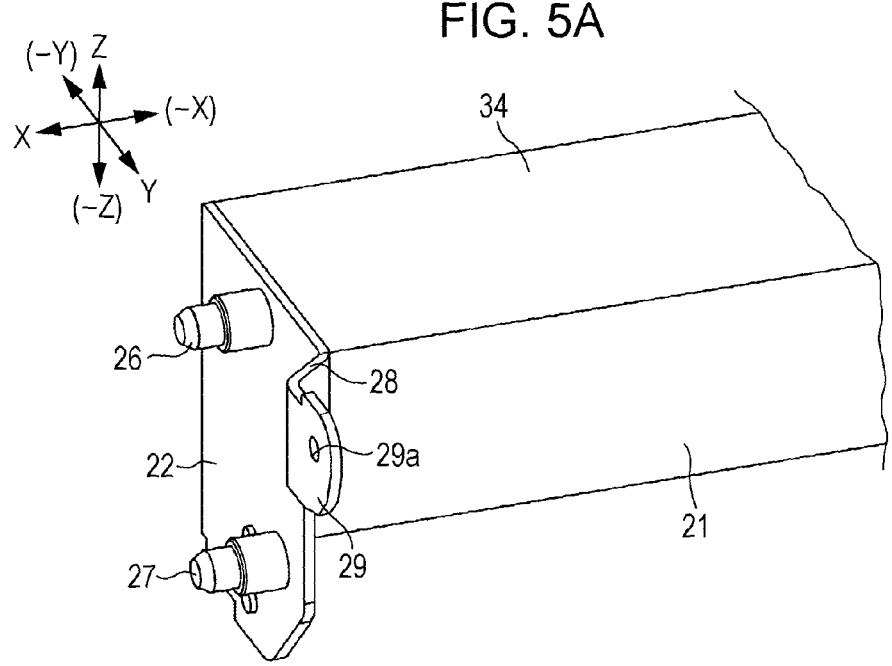
FIGS. 5A and 5B are enlarged explanatory views showing a specific portion of the sensor bracket according to the first exemplary embodiment, FIG. 5A being an enlarged explanatory view showing a specific portion of a front end portion of the sensor bracket, FIG. 5B being an enlarged explanatory view showing a specific portion of a rear end portion of the sensor bracket.
Figure 5B:
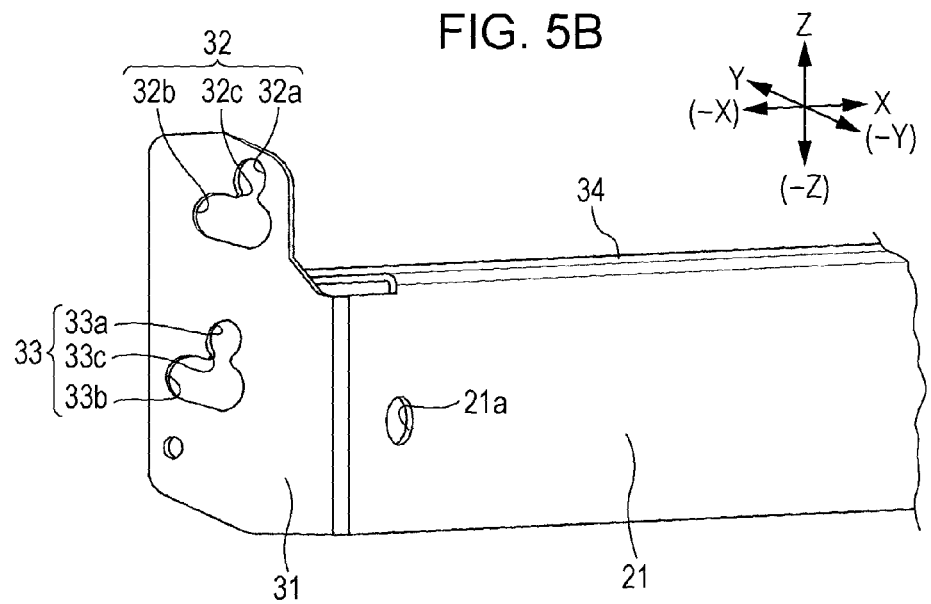

FIGS. 5A and 5B are enlarged explanatory views showing a specific portion of the sensor bracket according to the first exemplary embodiment, FIG. 5A being an enlarged explanatory view showing a specific portion of a front end portion of the sensor bracket, FIG. 5B being an enlarged explanatory view showing a specific portion of a rear end portion of the sensor bracket.

In FIGS. 1 to 3B, and 5A and 5B, a sensor bracket BR, which is an example of a supported portion body, is arranged outside the sensor unit U3. In FIGS. 3A, 3B, 5A, and 5B, the sensor bracket BR of the first exemplary embodiment includes a flat-plate-like left plate 21 as an example of a left plate portion. The left plate 21 is arranged at the left side of the unit frame 1 and extends in the front-rear direction. A third screw hole 21a is formed in a rear end portion of the left plate 21, at a position corresponding to the third coupling hole 13f.

In FIGS. 3A, 3B, and 5A, the sensor bracket BR includes a flat-plate-like front plate 22, which is an example of a first-end supported portion and an example of a front plate portion. The front plate 22 is arranged at the front side of the unit frame 1 and is formed by being bent rightward from a front end of the left plate 21.

In FIG. 3B, an upper pin 23, which is an example of an upper positioning portion and an example of an upper protrusion, and a lower pin 24, which is an example of a lower positioning portion and an example of a lower protrusion, are formed on a rear surface of the front plate 22. The upper pin 23 protrudes rearward and corresponds to the upper positioned hole 7a. The lower pin 24 is arranged below the upper pin 23, protrudes rearward, and corresponds to the lower positioned long hole 7b. Also, in FIGS. 3A and 5A, an upper front stud 26, which is an example of a first upper protruding portion, and a lower front stud 27, which is an example of a first lower protruding portion, are formed on a front surface of the front plate 22. The upper front stud 26 protrudes forward. The lower front stud 27 is arranged at the obliquely lower right side of the upper front stud 26 and protrudes forward.

The upper front stud 26 and the lower front stud 27 define a first protruding portion 26+27 of the first exemplary embodiment.

In FIGS. 3A, 3B, and 5A, a right extension portion 28 is formed at an upper portion of a right end of the front plate 22. The right extension portion 28 is formed by being bent forward to extend to the obliquely front right side. A fixed portion 29 is formed at a right end of the right extension portion 28. The fixed portion 29 is formed by being bent rightward to be parallel to the front plate 22. A fourth coupling hole 29a is formed in a center portion of the fixed portion 29. The fixed portion 29 of the first exemplary embodiment is arranged at the rear side with respect to front ends of the studs 26 and 27.

In the first exemplary embodiment, positioning in the up-down direction and left-right direction is performed when the upper pin 23 and the lower pin 24 penetrate through the upper positioned hole 7a and the lower positioned long hole 7b, and positioning and fixing in the left-right direction are performed when the third coupling hole 13f is clamped by a third screw (not shown), which penetrates through the third coupling hole 13f and the third screw hole 21a from the right side. Accordingly, the sensor unit U3 is fixed and supported at the sensor bracket BR.

In other words, in the first exemplary embodiment, the unit supported portion 7a+7b+13f of the sensor unit U3 is supported by a unit supporting portion 23+24+21a, which is an example of a sensor member support and is formed of the upper pin 23, the lower pin 24, the third screw hole 21a, and the third screw.

In FIGS. 3A, 3B, and 5B, the sensor bracket BR includes a flat-plate-like rear plate 31 as an example of a second-end supported portion and an example of a rear plate portion. The rear plate 31 is arranged at the rear side of the unit frame 1. The rear plate 31 is formed by being bent rightward from a rear end of the left plate 21, and extends upward by a larger length than a length of the left plate 21. The rear plate 31 has an upper rear positioning hole 32, and a lower rear positioning hole 33 that is arranged at the obliquely lower right side of the upper rear positioning hole 32. The rear positioning holes 32 and 33 have circular-hole-like upper through holes 32a and 33a, as examples of positioning portions. Also, lower long through holes 32b and 33b are formed below the upper through holes 32a and 33a. The lower long through holes 32b and 33b are examples of insertion portions and extend in the left-right direction. Further, coupling holes 32c and 33c are formed respectively between the upper through holes 32a and 33a and the lower long through holes 32b and 33b. The coupling holes 32c and 33c are examples of pass portions and respectively connect the holes 32a and 32b, and the holes 33a and 33b.

In the first exemplary embodiment, the lower long through holes 32b and 33b each have a pass width, which is a width in the up-down direction and is larger than a width in the left-right direction of the upper through hole 32a and a diameter of the upper through hole 33a. The coupling holes 32c and 33c each have a width in the left-right direction, which is smaller than the width in the left-right direction of the upper through hole 32a and the diameter of the upper through hole 33a.

The upper rear positioning hole 32 and the lower rear positioning hole 33 define a second recess portion 32+33 of the first exemplary embodiment.

In FIGS. 3A, 3B, 5A and 5B, the sensor bracket BR includes a flat-plate-like upper plate 34, which is an example of an upper plate portion. The upper plate 34 is arranged above the unit frame 1 and is formed by being bent rightward from an upper end of the left plate 21. A rear extension portion 34a is formed at a right portion of a rear end of the upper plate 34. The rear extension portion 34a extends rearward toward the rear plate 31.

Figure 6:
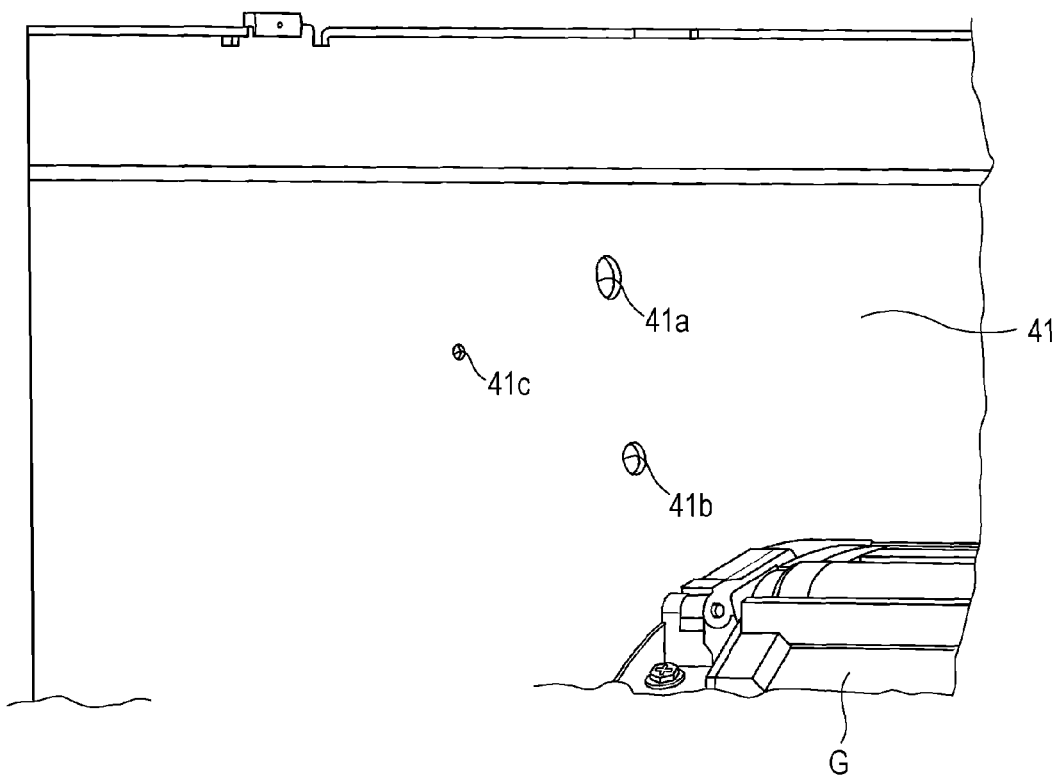
FIG. 6 is an enlarged explanatory view showing a specific portion of a front support according to the first exemplary embodiment.

FIG. 6 is an enlarged explanatory view showing a specific portion of a front support of the first exemplary embodiment.

Figure 7A:
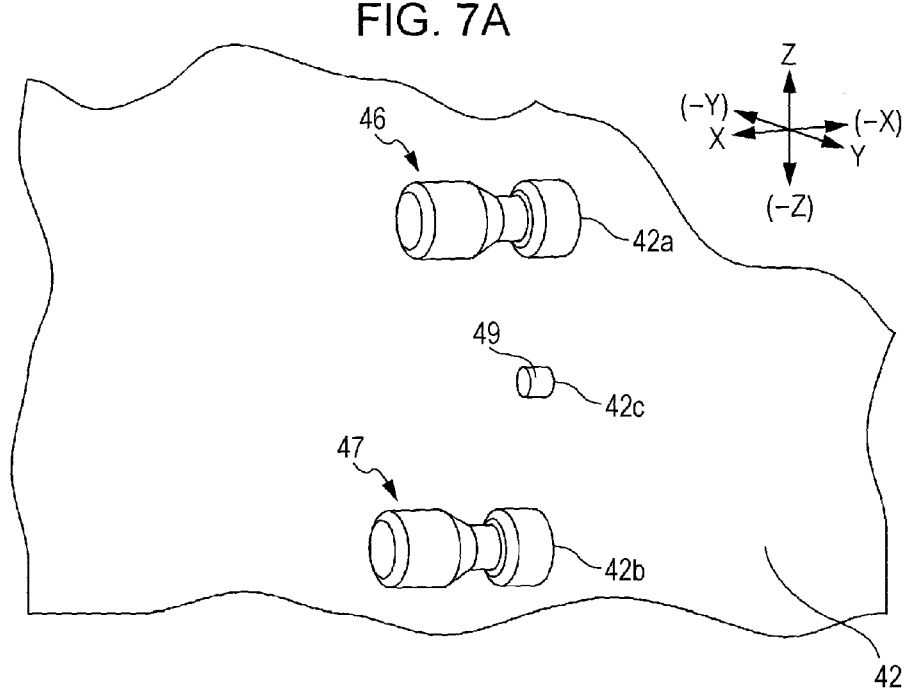
FIGS. 7A and 7B are enlarged explanatory views showing a specific portion of a rear support according to the first exemplary embodiment, FIG. 7A being an enlarged view of the rear support when rear studs are inserted, FIG. 7B being an enlarged view of the rear studs.
Figure 7B:
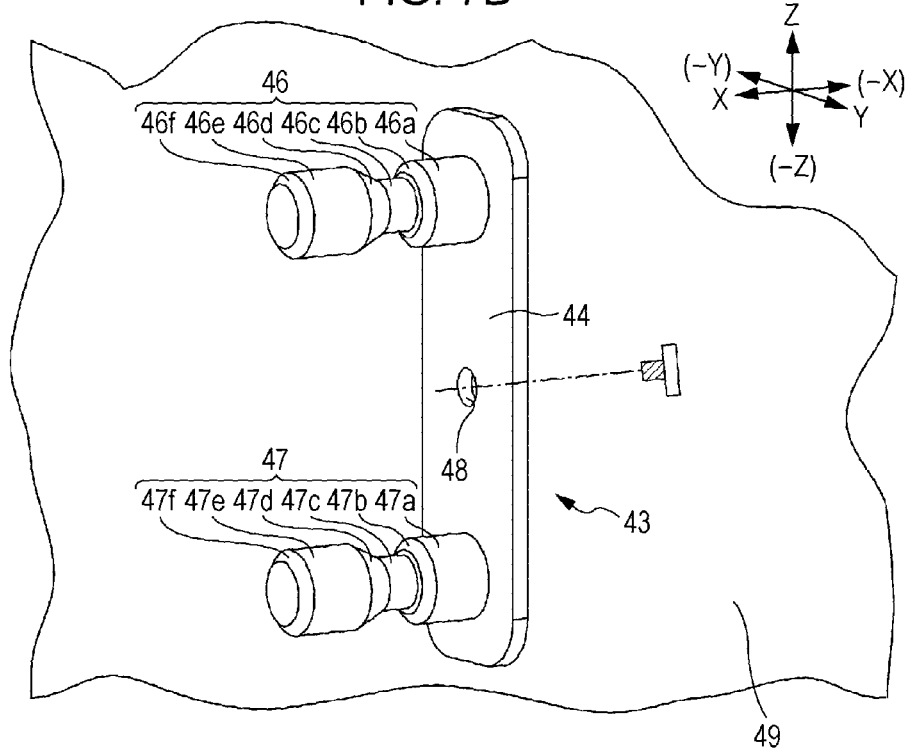

FIGS. 7A and 7B are enlarged explanatory views showing a specific portion of a rear support according to the first exemplary embodiment, FIG. 7A being an enlarged view of the rear support when rear studs are inserted, FIG. 7B being an enlarged view of the rear studs.

Figure 8A:
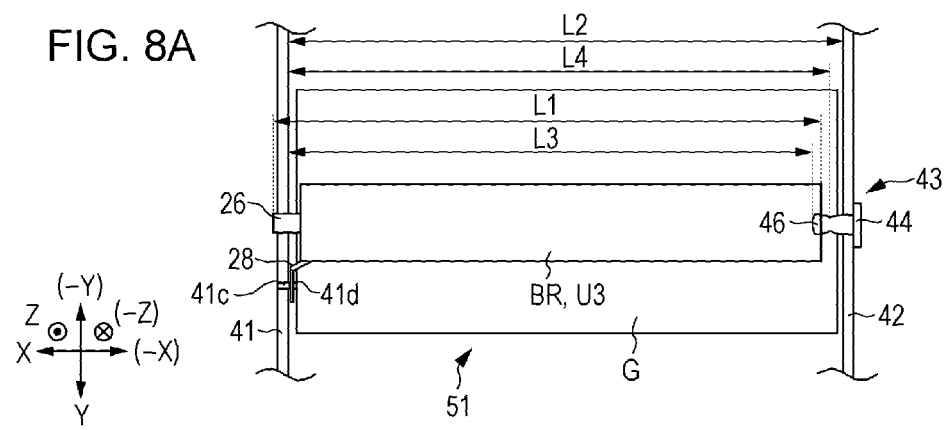
FIGS. 8A to 8C are explanatory views relating to arrangement of the respective supports and the sensor bracket according to the first exemplary embodiment, FIG. 8A being an explanatory view when an open/close cover is opened and a sensor housing space between the front and rear supports is viewed from the upper side, FIG. 8B being an explanatory view when a state in which the rear studs of the rear support are inserted into rear positioning holes of the sensor bracket and the sensor bracket extends from the rear support in an inclined manner toward the obliquely upper right side with respect to the front-rear direction is viewed from the upper side, FIG. 8C being an explanatory view when the state in FIG. 8B is viewed from the right side.
Figure 8B:
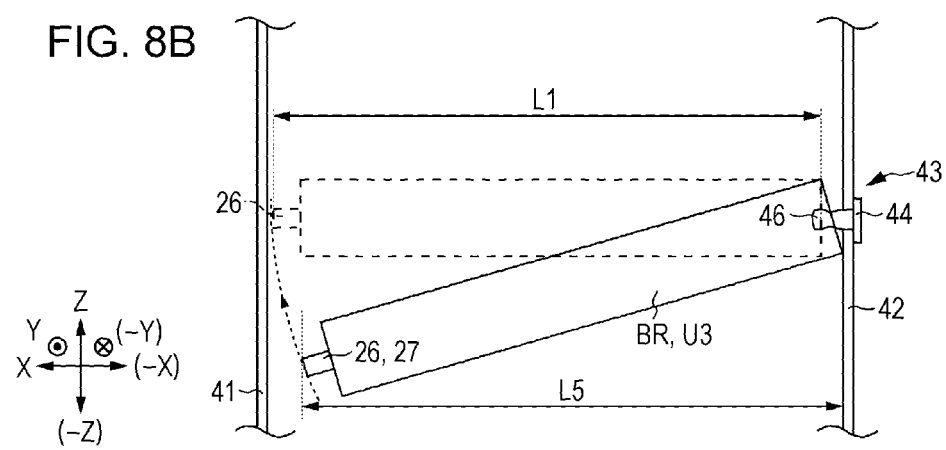
Figure 8C:
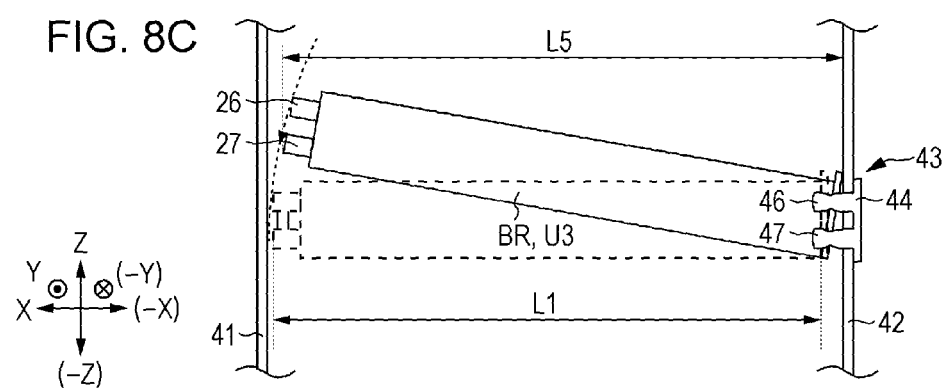

FIGS. 8A to 8C are explanatory views relating to arrangement of the respective supports and the sensor bracket according to the first exemplary embodiment, FIG. 8A being an explanatory view when an open/close cover is opened and a sensor housing space between the front and rear supports is viewed from the upper side, FIG. 8B being an explanatory view when a state in which the rear studs of the rear support are inserted into rear positioning holes of the sensor bracket and the sensor bracket extends from the rear support in an inclined manner toward the obliquely upper right side with respect to the front-rear direction is viewed from the upper side, FIG. 8C being an explanatory view when the state in FIG. 8B is viewed from the right side.

Referring to FIGS. 6 to 8C, a plate-like front support 41 and a plate-like rear support 42 are arranged at the front and rear sides of the sensor bracket BR. The front support 41 is an example of a first-end support and is arranged at the front side of the printer body U1. The rear support 42 is an example of a second-end support and is arranged at the rear side of the printer body U1.

In FIG. 6, the front support 41 of the first exemplary embodiment has a first upper long through hole 41a extending in the up-down direction at a position corresponding to the upper front stud 26, and a first lower through hole 41b arranged below the first upper long through hole 41a at a position corresponding to the lower front stud 27.

In the first exemplary embodiment, the first upper long through hole 41a has a width in the left-right direction that is previously determined in accordance with an outer diameter of the upper front stud 26 such that the upper front stud 26 is able to penetrate through the first upper long through hole 41a. Also, the first lower through hole 41b has an outer diameter that is previously determined in accordance with an outer diameter of the lower front stud 27 such that the lower front stud 27 is able to penetrate through and to be fitted to the first lower through hole 41b.

The first upper long through hole 41a and the first lower through hole 41b define a first recess portion 41a+41b of the first exemplary embodiment.

Also, the front support 41 has a fourth screw hole 41c as an example of a fixing portion. The fourth screw hole 41c is arranged at the right side of the first upper long through hole 41a at a position corresponding to the fourth coupling hole 29a. Hence, as shown in FIGS. 8A to 8C, by coupling the fourth coupling hole 29a and the fourth screw hole 41c together by using a fourth screw 41d which penetrates through these holes from the rear side, the front support 41 and the fixed portion 29 of the sensor bracket BR are fixed.

In FIG. 7A, the rear support 42 of the first exemplary embodiment has a second upper through hole 42a that penetrates through the rear support 42 in the front-rear direction at a position corresponding to the upper rear positioning hole 32 of the sensor bracket BR. Also, a second lower through hole 42b is formed below the second upper through hole 42a, and penetrates through the rear support 42 in the front-rear direction at a position corresponding to the lower rear positioning hole 33 of the sensor bracket BR.

Further, a fifth screw hole 42c is formed between the second upper through hole 42a and the second lower through hole 42b.

In FIGS. 7A and 7B, a rear through member 43 is supported on a rear surface of the rear support 42. In FIG. 7B, the rear through member 43 of the first exemplary embodiment includes a flat-plate-like fixed plate portion 44 that faces the rear support 42. An upper rear stud 46, as an example of a second upper protruding portion, is formed on a front surface of the fixed plate portion 44. The upper rear stud 46 penetrates through the second upper through hole 42a and protrudes forward. Also, a lower rear stud 47, as an example of a second lower protruding portion, is formed below the upper rear stud 46. The lower rear stud 47 penetrates through the second lower through hole 42b and protrudes forward.

Further, a fifth coupling hole 48 is formed between the rear studs 46 and 47. The fifth coupling hole 48 penetrates through the fixed plate portion 44 in the front-rear direction at a position corresponding to the fifth screw hole 42c. As shown in FIGS. 7A and 7B, by clamping the fifth coupling hole 48 by using a fifth screw 49, which penetrates through the fifth coupling hole 48 from the rear side, the rear support 42 and the rear through member 43 are fixed.

The upper rear stud 46 and the lower rear stud 47 define a second protruding portion 46+47 of the first exemplary embodiment.

The rear studs 46 and 47 of the first exemplary embodiment have circular cylindrical, or substantially circular cylindrical rear circular cylinder portions 46a and 47a that extend forward from the front surface of the fixed plate portion 44. Rear circular truncated cone portions 46b and 47b, which are examples of circular-truncated-cone-like rear circular truncated cone portions, are formed at front ends of the rear circular cylinder portions 46a and 47a. The rear circular truncated cone portions 46b and 47b have outer diameters that decrease toward the front side. Center circular cylinder portions 46c and 47c that extend forward are formed at front ends of the rear circular truncated cone portions 46b and 47b. Front circular truncated cone portions 46d and 47d, which are examples of circular-truncated-cone-like front circular truncated cone portions, are formed at front ends of the center circular cylinder portions 46c and 47c. The front circular truncated cone portions 46d and 47d have outer diameters that increase toward the front. Front circular cylinder portions 46e and 47e that extend forward are formed at front ends of the front circular truncated cone portions 46d and 47d. Chamfers 46f and 47f are formed at edges of front end surfaces of the front circular cylinder portions 46e and 47e of the first exemplary embodiment.

In the first exemplary embodiment, the front circular cylinder portions 46e and 47e have outer diameters that are equivalent to outer diameters of the rear circular cylinder portions 46a and 47a. Also, the large-diameter circular cylinder portions 46a, 46e, 47a, 47e have outer diameters that are determined in accordance with outer diameters of the upper through holes 32a and 33a. The circular cylinder portions 46a, 46e, 47a, and 47e may penetrate through and be fitted to the upper through holes 32a and 33a. The small-diameter center circular cylinder portions 46c and 47c have outer diameters that are previously determined in accordance with widths in the left-right direction of the coupling holes 32c and 33c. The center circular cylinder portions 46c and 47c may pass through the coupling holes 32c and 33c in the up-down direction while being fitted to the coupling holes 32c and 33c. The outer diameters of the circular cylinder portions 46a, 46e, 47a, and 47e are larger than the widths of the coupling holes 32c and 33c, and hence do not pass through the coupling holes 32c and 33c.

The center circular cylinder portions 46c and 47c define a small-diameter first circular cylinder portion 46c+47c. The circular cylinder portions 46a, 46e, 47a, and 47e define a large-diameter second circular cylinder portion 46a+46e+47a+47e.

In FIGS. 8A to 8C, a sensor housing space 51, which is an example of an inner space of the printer body U1, is formed between the front support 41 and the rear support 42. In FIG. 8A, according to the first exemplary embodiment, when L1 [mm] is a length in the front-rear direction from front ends of the front studs 26 and 27 of the front plate 22 to the rear plate 31, i.e., a bracket length, which is an example of a first length that is a length in the front-rear direction of the sensor bracket BR; L2 [mm] is a length in the front-rear direction from the rear surface of the front support 41 to the front surface of the rear support 42, i.e., a space length, which is an example of a second length that is a length in the front-rear direction of the sensor housing space 51; L3 [mm] is a positioning length, which is an example of a third length that is a length from the rear surface of the front support 41 to the front ends of the front circular cylinder portions 46e and 47e of the rear studs 46 and 47; and L4 [mm] is a pass length, which is an example of a fourth length that is a length in the front-rear direction from the rear surface of the front support 41 to the center circular cylinder portions 46c and 47c of the rear studs 46 and 47, these lengths satisfy a condition of (positioning length L3)<(bracket length L1)<(pass length L4)<(space length L2).

In FIGS. 8B and 8C, according to the first exemplary embodiment, when the rear studs 46 and 47 of the rear support 42 are inserted into the lower long through holes 32b and 33b of the rear positioning holes 32 and 33 of the sensor bracket BR, a front end portion of the sensor bracket BR may be inclined with respect to the front-rear direction. When L5 [mm] is an inclined bracket length, which is an example of a first inclination length that is a length in the front-rear direction from the front end to the rear end of the inclined sensor bracket BR, and which is an example of a variable length, if inclination degree of the sensor bracket BR is large, these lengths satisfy a condition of (inclined bracket length L5)< (positioning length L3), or if the inclination degree of the sensor bracket BR is small, these lengths satisfy a condition of (inclined bracket length L5)≧(positioning length L3). The inclined bracket length L5 of the first exemplary embodiment constantly satisfies a condition of (inclined bracket length L5)<(bracket length L1) while the rear studs 46 and 47 are inserted into the lower long through holes 32b and 33b.

Action of First Exemplary Embodiment

In the printer U of the first exemplary embodiment including the above-described configuration, if a job is executed, a latent image is developed on the surface of the image holding member PR in the development region Q2 with the toner of each of the respective colors held by the development rollers GRy to GRk of the developing units GY to GK when each of the developing units GY to GK stops at the development position P1. At this time, the toner of each of the developing units GY to GK is consumed in accordance with the toner image on the surface of the image holding member PR. In the printer U, as shown in FIGS. 1 and 2, the sensor bodies 6 of the sensor unit U3 that faces each of the development rollers GRy to GRk of the developing units GY to GK when each of the development units GY to GK stops at the detection position P2 detect the density of the toner on the surface of each of the development rollers GRy to GRc, and estimate the density of the toner in each of the development containers GHy to GHc based on the detection result of the sensor bodies 6. Then, when each of the development units GY to GC of the respective colors of Y, M, and C rotationally moves from the detection position P2 to the development position P1 and is supplied with the developer from the toner cartridge, the supply amount of the developer is adjusted in accordance with the estimated toner density.

Figure 9:
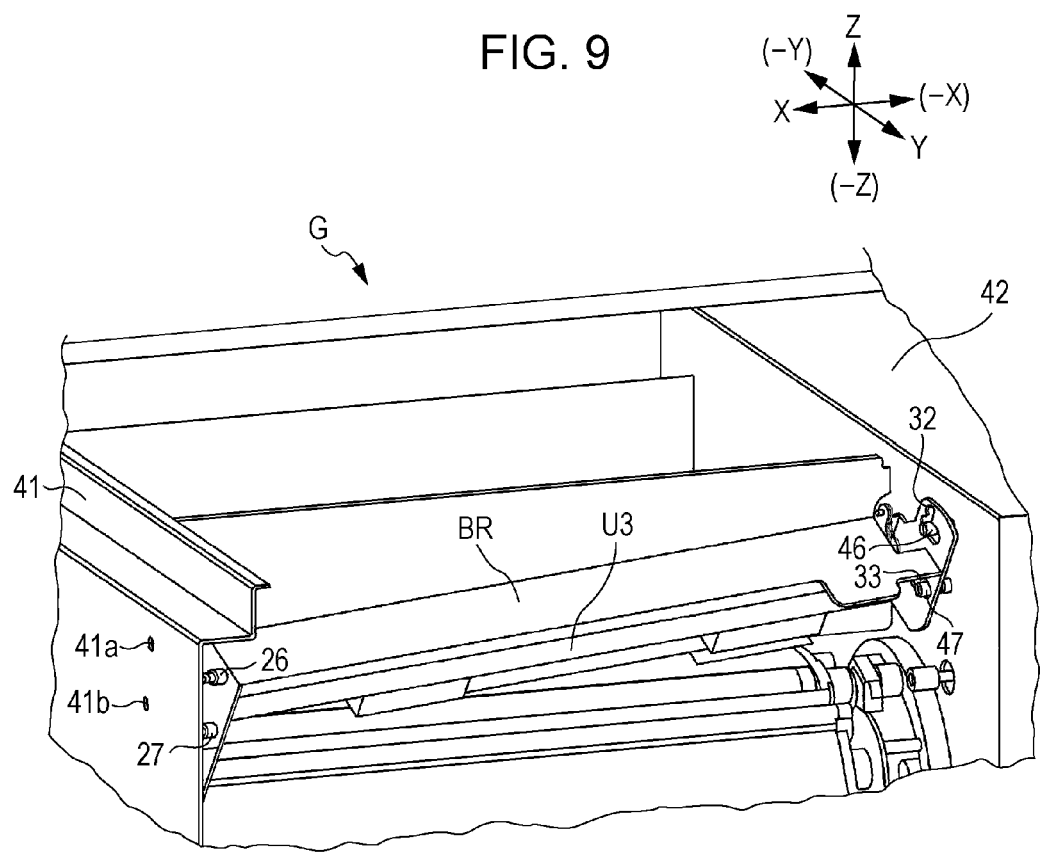
FIG. 9 is an action explanatory view of the first exemplary embodiment, FIG. 9 being an enlarged perspective view showing a specific portion in a state in which the sensor bracket is advanced into the sensor housing space while being inclined with respect to the front-rear direction.

FIG. 9 is an action explanatory view of the first exemplary embodiment, FIG. 9 being an explanatory view in a state in which the sensor bracket is advanced into the sensor housing space while being inclined with respect to the front-rear direction.

FIG. 10 is an explanatory view showing a specific portion in a sate in which the front side of the sensor bracket is moved from the state in FIG. 9 and the sensor bracket is arranged perpendicularly to the front and rear supports.

FIG. 11 is an explanatory view in a state in which the sensor bracket is moved upward from the state in FIG. 10 and hence the rear studs pass through coupling holes and penetrate through upper through holes.

FIG. 12 is an explanatory view of a state in which the sensor bracket is moved forward from the state in FIG. 11 and hence the studs at both front and rear ends respectively penetrate through the through holes, are fitted to the through holes, and are positioned.

Figure 13:
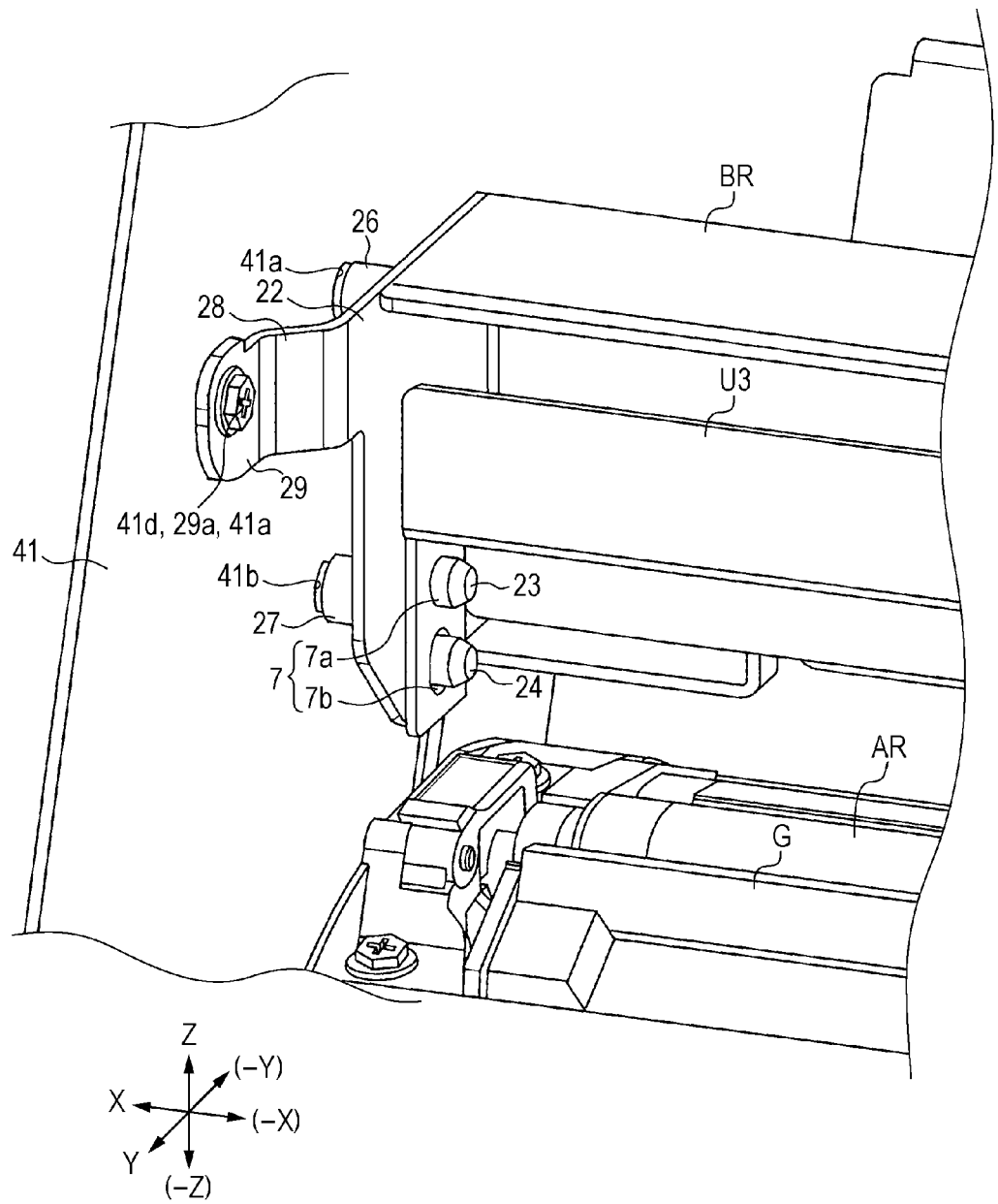
FIG. 13 is an explanatory view when the state in FIG. 12 is changed to a state in which a fixed portion of the sensor bracket is fixed by screwing and hence the sensor bracket is fixed to the front support.

FIG. 13 is an explanatory view when the state in FIG. 12 is changed to a state in which a fixed portion of the sensor bracket is fixed by screwing and hence the sensor bracket is fixed to the front support.

The sensor unit U3 of the first exemplary embodiment is detachably supported by the supports 41 and 42 of the printer body U1 via the sensor bracket BR. In the first exemplary embodiment, if an entire unit U3+BR, which is an example of a sensor member, is mounted, the open/close cover U2 is opened and the upper side of the sensor housing space 51 is exposed. In this state, the entire unit U3+BR is advanced from the upper side of the sensor housing space 51, and the rear studs 46 and 47 of the rear support 42 are inserted into the lower long through holes 32b and 33b of the rear positioning holes 32 and 33 of the sensor bracket BR. At this time, the entire unit U3+BR of the first exemplary embodiment satisfies the condition of (bracket length L1)<(space length L2). The sensor bracket BR may be advanced to the sensor housing space 51 in a state in which the sensor bracket BR extends perpendicularly to the supports 41 and 42, i.e., the sensor bracket BR extends in the front-rear direction.

However, since the entire unit U3+BR of the first exemplary embodiment satisfies the condition of (positioning length L3)<(bracket length L1), the rear plate 31 of the sensor bracket BR may interfere with the upper rear stud 46 of the rear support 42. The entire unit U3+BR is not able to be mounted.

Hence, to mount the entire unit U3+BR, the entire unit U3+BR is inclined to satisfy the condition of (inclined bracket length L5)<(positioning length L3). Accordingly, the rear studs 46 and 47 are inserted into the lower long through holes 32b and 33b of the rear positioning holes 32 and 33 while both the front and rear end portions of the sensor bracket BR do not interfere with the supports 41 and 42.

Consequently, the front end portion of the sensor bracket BR is brought into a state shown in FIG. 9 in which the front end portion of the sensor bracket BR is arranged in the sensor housing space 51 in an inclined manner toward the right side with respect to the front-rear direction.

Also, the lower long through holes 32b and 33b of the first exemplary embodiment are long holes, and hence the rear studs 46 and 47 inserted into the lower long through holes 32b and 33b are movable in the front-rear direction and the left-right direction. Accordingly, while the rear studs 46 and 47 are fitted into the lower long through holes 32b and 33b, the front end portion of the sensor bracket BR is rotationally movable around the rear end portion of the sensor bracket BR. If the front end portion of the sensor bracket BR rotationally moves leftward from the state shown in FIG. 9, the inclination degree of the sensor bracket BR decreases. In this case, the entire unit U3+BR of the first exemplary embodiment satisfies a condition of (positioning length L3)<(inclined bracket length L5)<(bracket length L1)<(pass length L4)<(space length L2). Accordingly, the front end portion of the sensor bracket BR is rotationally movable while the rear studs 46 and 47 are not removed from the lower long through holes 32b and 33b and the front end portion of the sensor bracket BR does not interfere with the support 41.

The sliding movement of the sensor bracket BR in the front-rear direction and the rotational movement of the front end portion of the sensor bracket BR to the left side are performed until the state shown in FIG. 9 becomes a state shown in FIG. 10 in which the center circular cylinder portions 46c and 47c of the rear studs 46 and 47 are fitted to the rear positioning holes 32 and 33 such that the rear studs 46 and 47 may pass through the coupling holes 32c and 33c of the rear positioning holes 32 and 33. In particular, when the front circular cylinder portions 46e and 47e of the rear studs 46 and 47 are fitted to the rear positioning holes 32 and 33 of the rear plate 31, the sensor bracket BR slides rearward. When the rear circular cylinder portions 46a and 47a of the rear studs 46 and 47 are fitted to the rear positioning holes 32 and 33, the sensor bracket BR slides forward. The entire unit U3+BR of the first exemplary embodiment satisfies the condition of (bracket length L1)<(pass length L4). Accordingly, the sensor bracket BR slides forward and is brought into the state shown in FIG. 10 without the front studs 26 and 27 interfering with the front support 41.

In the state shown in FIG. 10, at the front side of the printer body U1, the front plate 22 of the sensor bracket BR faces the rear surface of the front support 41, and the front studs 26 and 27 are arranged at obliquely lower positions of the first upper long through hole 41a and the first lower through hole 41b.

Then, when the sensor bracket BR slides downward, the center circular cylinder portions 46c and 47c pass through the upper coupling holes 32c and 33c, and the rear studs 46 and 47 move from the lower long through holes 32b and 33b to the upper through holes 32a and 33a. Consequently, the sensor bracket BR moves to attain a state shown in FIG. 11 in which the front circular cylinder portions 46e and 47e of the rear studs 46 and 47 face the upper through holes 32a and 33a at the front side of the upper through holes 32a and 33a, and the front studs 26 and 27 faces the first recess portion 41a and the first lower through hole 41b at the rear side of the first recess portion 41a and the first lower through hole 41b.

Then, when the sensor bracket BR slides forward, at the front side, the front studs 26 and 27 penetrate through and are fitted to the holes 41a and 41b of the front support 41. At the rear side, the front circular cylinder portions 46e and 47e penetrate through and are fitted to the upper through holes 32a and 33a while the upper through holes 32a and 33a are guided by the front circular truncated cone portions 46d and 47d when the upper through holes 32a and 33a slide between the center circular cylinder portions 46c and 47c and the front circular cylinder portions 46e and 47e.

Consequently, a state of the entire unit U3+BR becomes a state shown in FIG. 12 in which the entire unit U3+BR is positioned at the supports 41 and 42. In this state, the rear surface of the front support 41 contacts the fixed portion 29 of the sensor bracket BR. As shown in FIG. 13, by coupling the fourth coupling hole 29a and the fourth screw hole 41c together by screwing, the front support 41 and the fixed portion 29 are fixed. Consequently, the entire unit U3+BR is fixed and supported while the entire unit U3+BR is positioned at the supports 41 and 42.

In the first exemplary embodiment, regarding the entire unit U3+BR extending in the front-rear direction, the studs 26+27 and 46+47 extending in the front-rear direction are inserted into the holes 41a+41b and 32+33 and are positioned at the supports 41 and 42. With a rotary developing device G, if a supply mechanism and a discharge mechanism of a developer are provided in the front-rear direction, the attachment/detachment in the front-rear direction is difficult. Also, the configuration may be complicated if all members in the printer body U1 are detachably attached in the front-rear direction. Hence, regarding the developing device G with the difficulty in attachment or detachment in the front-rear direction, the configuration in which the attachment or detachment is carried out from the upper side or in the left-right direction.

When the developing device G etc. is attached or detached from the upper side or in the left-right direction, other members such as a sensor unit U3 located near the developing device G may not be arranged in a direction other than the attachment/detachment direction. For example, in the printer U of the first exemplary embodiment, the entire unit U3+BR may be supported at a position not above the developing device G but below the developing device G in a non-detachable manner, to prevent the entire unit U3+BR from disturbing replacement work of the developing device G. Therefore, a configuration in which the entire unit U3+BR is detachably attached is required in the pass region of the developing device G for the replacement work of the developing device G.

Positioning of the entire unit U3+BR during attachment or detachment is performed by using the studs and holes as described above because the configuration is simple and accuracy is easily secured. If a stud protruding to the upper side or in the left-right direction is provided for the unit U3+BR that is attached or detached from the upper side or in the left-right direction, a fixed flange with a stud or a hole is arranged at the printer body U1 in the pass region of the developing device G. The stud or hole may disturb the attachment/detachment work of the developing device G.

Therefore, in the first exemplary embodiment, a stud or a hole is provided in front and rear frames (41, 42) that are intersect with the upward direction or left-right direction which is the attachment/detachment direction. However, if the stud protrudes in the front-rear direction, after the entire unit U3+BR is mounted from the upper side or in the left-right direction, the entire unit U3+BR has to be moved in the front-rear direction, so that the stud is fitted into the hole.

In this case, if the distance (L2) between the front and rear frames (41, 42) is sufficiently large, the stud is easily fitted to the hole. However, the size of the printer U may be increased.

Owing to this, while the sensor bracket BR is inclined, in the first exemplary embodiment, the rear stud 46+47 is inserted into the hole 32+33, and while the rear studs 46 and 47 are inserted, the inclined sensor bracket BR rotationally moves and slides, and hence the studs 26+27, and 46+47 protruding in the front-rear direction are fitted to the holes 41a+41b, and 32+33.

Figure 14A:
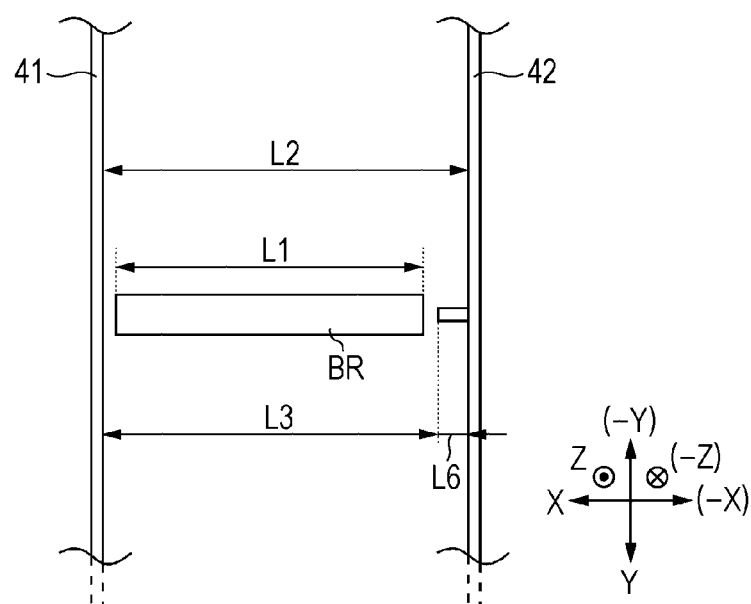
FIGS. 14A and 14B are action explanatory views according to the first exemplary embodiment, FIG. 14A being an explanatory view of a configuration in which the sensor bracket is housed without being inclined and then slid, and hence the studs are inserted into the holes, FIG. 14B being an explanatory view of a configuration according to the first exemplary embodiment, in which the sensor bracket is slid with being inclined and the studs are inserted into the holes.
Figure 14B:
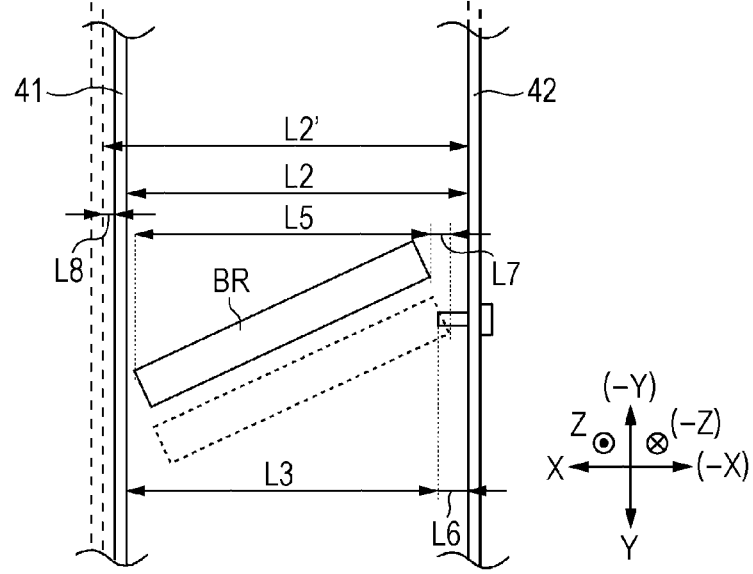

FIGS. 14A and 14B are action explanatory views according to the first exemplary embodiment, FIG. 14A being an explanatory view of a configuration in which the sensor bracket is housed without being inclined and then slid, and hence the studs are inserted into the holes, FIG. 14B being an explanatory view of a configuration according to the first exemplary embodiment, in which the sensor bracket is slid with being inclined and the studs are inserted into the holes.

As shown in FIG. 14A, a configuration is considered in which an entire unit U3+BR is advanced to a space between supports 41 and 42 from the upper side while the entire unit U3+BR is not inclined, and then a sensor bracket BR slides and a stud extending in the front-rear direction is inserted into a hole. In this case, if L2' [mm] is the space length, and L6 [mm] is a stud length, which is an example of a sixth length that is a length of each of rear studs 46 and 47 in the front-rear direction, these lengths have to satisfy a condition of (bracket length L1)+(stud length L6)<(space length L2').

In contrast, as shown in FIG. 14B, with the configuration of the first exemplary embodiment, to insert the rear stud 46+47 into the hole 32+33 while the sensor bracket BR is inclined, a condition of (inclined bracket length L5)+(stud length L6)< (space length L2) has to be satisfied. Also, when L7 [mm] is a movement distance, which is an example of a seventh length that is a length in the front-rear direction when the rear studs 46 and 47 are inserted and the sensor bracket BR moves rearward, to arrange the inclined sensor bracket BR to the state shown in FIG. 10 through the rotational movement and sliding movement, a condition of (bracket length L1)+(stud length L6)−(movement length L7)<(space length L2) has to be satisfied.

In the first exemplary embodiment, as shown in FIGS. 8A to 8C, conditions of (stud length L6)=(space length L2)−(positioning length L3), (movement length L7)≈(pass length L4)−(positioning length L3), and (inclined bracket length L5)<(positioning length L3)<(bracket length L1)<(pass length L4)<(positioning length L3) are satisfied; based on the condition of (inclined bracket length L5)<(positioning length L3), a condition of (inclined bracket length L5)+{(space length L2)−(positioning length L3)}<(space length L2) is established; and based on the condition of (bracket length L1)<(pass length L4), a condition of (bracket length L1)+{(space length L2)−(positioning length L3)}−{(pass length L4)−(positioning length L3)}<(space length L2) is established. That is, in the first exemplary embodiment, conditions of (inclined bracket L5)+(stud length L6)<(space length L2), and (bracket length L1)+(stud length L6)−(movement length L7)<(space length L2) are satisfied.

Hence, when L8 [mm] is a difference length, which is an example of an eighth length, between the space length L2' of the configuration shown in FIG. 14A and the space length L2 of the first exemplary embodiment shown in FIG. 14B, a condition of (difference length L8)=(space length L2')−(space length L2)=(movement length L7) is established. Consequently, the printer body U1 of the first exemplary embodiment may have the space length L2 that is smaller than that of the configuration shown in FIG. 14A by a length corresponding to the movement length L7.

In particular, in the printer U of the first exemplary embodiment, the space length L2 may be small within a range that allows the inclined sensor bracket BR to rotate and slide. As compared with the configuration shown in FIG. 14A having the large space length L2, the size of the printer body U1 may be decreased in the front-rear direction. Consequently, in the printer U of the first exemplary embodiment, even if the entire unit U3+BR is attached or detached from the upper side, the printer U does not become excessively large.

Also, in the first exemplary embodiment, when the entire unit U3+BR is attached to the supports 41 and 42, the studs 26+27 and 46+47 extending in the front-rear direction are fitted to the holes 41a+41b and 32+33 and are positioned. Consequently, in the printer U of the first exemplary embodiment, even if the configuration in which the entire unit U3+BR is attached and detached from the upper side, the sensor unit U3 is accurately positioned like a configuration in which the entire unit is attached or detached from the front side and the stud extending in the front-rear direction is fitted to the hole.

Further, in the first exemplary embodiment, during the replacement for the developing device G, the sensor bracket BR and the developing device G may be removed from the upper side or the lateral side of the sensor housing space 51 in that order. Accordingly, with the printer U of the first exemplary embodiment, the troublesome situation of the replacement work of the developing device G is reduced, and maintenance performance of the printer body U1 is enhanced.

Consequently, the printer U of the first exemplary embodiment increases positioning accuracy of the sensor unit U3, decreases the size of the printer body U1, and enhances the maintenance performance.

Also, in the first exemplary embodiment, as shown in FIGS. 8A and 13, the front support 41 and the fixed portion 29 of the sensor bracket BR are coupled together by screwing, so that the positioning of the entire unit U3+BR is not shifted.

Also, the fixed portion 29 of the first exemplary embodiment extends from the front plate 22 and is arranged at the obliquely upper right side of the developing rollers GRy to GRk at the detection position P2. The fixed portion 29 is coupled at the outside of an image formation width AR that is previously determined at a center portion in the front-rear direction of each of the development rollers GRy to GRk as shown in FIG. 12. Consequently, in the printer U of the first exemplary embodiment, chips and dusts of the fixed portion 29 and the fourth screw hole 41c generated as the result of screwing are hardly dropped in the range of the image formation width AR on each of the surfaces of the development rollers GRy to GRk. Accordingly, when each of the developing units GY to GK rotationally moves to the development position P1 for the development and transfer, the chips and dusts dropped on the development rollers GRy to GRk are prevented from entering the development region Q2 and from causing an image defect etc.

Modifications

The exemplary embodiment of the present invention has been described above; however, the present invention is not limited to the exemplary embodiment, and may be modified in various forms within the scope of the present invention described in the claims. Modifications (H01) to (H016) of the present invention are exemplarily described below.

(H01) In the exemplary embodiment, the printer U has been described as an example of an image forming apparatus. However, it is not limited thereto. The image forming apparatus may be a copier, a facsimile, or a multi-function apparatus including plural functions of, for example, copy and facsimile. The image forming apparatus is not limited to an image forming apparatus of an electrophotographic system, and may be of any image forming system, such as an inkjet recording system, a thermal head system, or a lithographic system. The image forming apparatus is not limited to an image forming apparatus of multi-color development, and may be of a single color, i.e., a monochrome color. The developing device G is not limited to a rotational developing device, and may be a configuration including an image holding member, a charging unit, a latent image forming device, a developing unit, etc., for each color. That is, the developing device may have a tandem configuration.

(H02) In the exemplary embodiment, the first protruding portion 26+27 is arranged at the sensor bracket BR, and the second protruding portion 46+47 is arranged at the rear support 42. However, it is not limited thereto, and the combination of arrangements of the protruding portions and recesses may be desirably changed. For example, the second protruding portion may be arranged at the sensor bracket BR and the first protruding portion may be arranged at the front support 41 in a reversed manner to the exemplary embodiment. Alternatively, for example, both front and rear protruding portions may be arranged at the sensor bracket BR, or both front and rear protruding portions may be arranged at the supports 41 and 42.

(H03) In the exemplary embodiment, the first protruding portion 26+27 is arranged at the front side of the printer body U1, and the second protruding portion 46+47 is arranged at the rear side of the printer body U1. However, it is not limited thereto, and the combination of arrangements of the protruding portions and recesses may be desirably changed. For example, the second protruding portion 46+47 may be arranged at the front side of the printer body U1, and the first protruding portion 26+27 may be arranged at the rear side of the printer body U1 in a reversed manner to the exemplary embodiment. In this case, the second recess portion 32+33 corresponding to the second protruding portion 46+47 having a special shape has to be arranged at the front side of the printer body U1.

(H04) in the exemplary embodiment, the rear studs 46 and 47 are formed at the rear through member 43 supported at the rear support 42. However, it is not limited thereto, and the rear studs 46 and 47 may be integrally formed with the rear support 42.

(H05) In the exemplary embodiment, the entire unit U3+BR extending in the front-rear direction is attached or detached from the upper side. However, it is not limited thereto. As long as the entire unit U3+BR does not disturb the other members in the printer body U1, the entire unit U3+BR may be attached or detached in any direction orthogonal to the front-rear direction. For example, if the open/close cover U2 is provided at the right side, the entire unit U3+BR may be attached and detached from the right side.

(H06) In the exemplary embodiment, the rear studs 46 and 47 are formed such that the outer diameters of the rear circular cylinder portions 46a and 47a are equivalent to the outer diameters of the front circular cylinder portions 46e and 47e. However, the outer diameters of the rear circular cylinder portions 46a and 47a are desirably changed. For example, the outer diameters of the rear circular cylinder portions 46a and 47a may be larger than the outer diameters of the front circular cylinder portions 46e and 47e, or may be equivalent to the outer diameters of the center circular cylinder portions 46c and 47c.

(H07) Like the exemplary embodiment, the circular truncated cone portions 46b, 47b, 46d, and 47d are desirably formed between the large-diameter circular cylinder portions 46a, 47a, 46e, and 47e and the small-diameter center circular cylinder portions 46c and 47c. However, the circular truncated cone portions 46b, 47b, 46d, and 47d may be omitted. Also, the chamfers 46f and 47f are desirably formed at the edges of the front end surfaces of the front circular cylinder portions 46e and 47e to allow the front circular cylinder portions 46e and 47e to be easily inserted into the lower long through holes 32b and 33b. However, the chamfers 46f and 47f may be omitted.

(H08) In the exemplary embodiment, as shown in FIG. 9, the rear studs 46 and 47 are inserted into the lower long through holes 32b and 33b of the rear positioning holes 32 and 33 while the front end portion of the sensor bracket BR is inclined to the right side with respect to the front-rear direction. However, the direction in which the front end portion of the sensor bracket BR is inclined during the insertion is not limited thereto, and the front end portion may be inclined in the up-down direction or to the left side.

(H09) In the exemplary embodiment, the sensor unit U3 detects only the toner density of each of the developing units GY to GC of Y, M, and C colors when each of the developing units GY to GC stops at the detection position P2. However, if a sensor unit U3 that is capable of detecting the toner density of black (K) is used, the sensor unit U3 may detect the toner density of each of the developing units GY to GK of all Y to K colors when each of the developing units GY to GK stops at the detection position P2.

(H010) In the exemplary embodiment, the sensor unit U3 is arranged above the developing device G and detects the toner densities of the development rollers GRy to GRc of the developing units GY to GC when each of the developing units GY to GC stops at the detection position P2. However, if there is a space where the sensor unit U3 may be arranged and the detection accuracy of the sensor unit U3 is sufficiently provided, the arrangement of the sensor unit U3 may be changed and the sensor unit U3 may detect the toner densities of the development rollers GRy to GRc of the developing units GY to GC when each of the developing units GY to GC stops at any of the stop positions P1, P3, and P4 other than P2. At this time, the entire unit U3+BR may be arranged beside or below the development rollers GRy to GRc depending on the stop position P1, P3, or P4. In this case, even if the fixed portion 29 is arranged at a position within the image formation width AR of each of the development rollers GRy to GRk, the chips and dusts of the fixed portion 29 and the fourth screw hole 41c are hardly dropped in the range of the image formation width AR.

(H011) In the exemplary embodiment, the first protruding portion 26+27 and the second protruding portion 46+47 each include two upper and lower studs. However, the number of studs is not limited thereto. For example, the first and second protruding portions each may include a single stud or three or more studs.

(H012) Like the exemplary embodiment, the fixed portion 29 that is screwed is arranged outside and above the image formation width AR of each of the development rollers GRy to GRk at the detection position P2 to prevent the chips and dusts of the fixed portion 29 and the fourth screw hole 41c from being dropped within the range of the image formation width AR. However, the fixed portion 29 may be arranged above the image formation width AR.

(H013) Regarding the entire unit U3+BR of the exemplary embodiment, the sensor unit U3 and the sensor bracket BR are separate members. However, it is not limited thereto, and the sensor unit U3 and the sensor bracket BR may be integrally formed.

(H014) Like the exemplary embodiment, regarding the first recess portion 41a+41b and the second recess portion 32+33, to allow the first protruding portion 26+27 and the second protruding portion 46+47 to be easily inserted, guided, and fit, the first protruding portion 26+27 and the second protruding portion 46+47 desirably have circular cylindrical shapes or substantially circular cylindrical shapes. However, it is not limited thereto, and for example, the first protruding portion 26+27 and the second protruding portion 46+47 may have prism-like shapes. In this case, the first recess portion 41a+41b and the second recess portion 32+33 have to be formed according to the shapes of the protruding portions 26+27 and 46+47 so that the protruding portions 26+27 and 46+47 are fit to the first recess portion 41a+41b and the second recess portion 32+33.

(H015) In the exemplary embodiment, the first recess portions 41a and 41b and the second recess portion 32+33 are through holes. However, it is not limited thereto, and for example, the first and second recess portions may be grooves or recesses.

(H016) In the exemplary embodiment, the sensor unit U3 detects the toner densities of the development rollers GRy to GRc. However, it is not limited thereto, and for example, the sensor unit U3 may detect the density on the intermediate transfer belt B.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An image forming apparatus, comprising:
a sensor member that is mounted in the image forming apparatus, detects a developer, has a first end and a second end opposite to each other in a longitudinal direction of the sensor member, and is supported by the first end, the second end, a first support structure of the image forming apparatus, and a second support structure of the image forming apparatus, the first support structure supporting the first end, the second support structure supporting the second end;
the first support structure including
one of a first protruding portion and a first recess portion, the first recess portion supporting the first protruding portion movably in the longitudinal direction of the sensor member, wherein the other one of the first protruding portion and the first recess portion is arranged in the first end of the sensor member; and
the second support structure including
one of a second protruding portion and a second recess portion, the second recess portion supporting the second protruding portion movably in a direction defined by connecting the first end and the second end, wherein the other one of the second protruding portion and the second recess portion is arranged in the second end of the sensor member, the second protruding portion having
a first cylinder portion that extends in a longitudinal direction of the second protruding portion, and
a second cylinder portion that is arranged at an end side of the second protruding portion next to the first cylinder portion, the second cylinder portion having a larger external shape than an external shape of the first cylinder portion and extending in the longitudinal direction of the second protruding portion, and
the second recess portion having
an insertion portion that allows the second protruding portion to be inserted, and that is larger than the external shape of the second cylinder portion,
a pass portion that is connected with the insertion portion, that is larger than the external shape of the first cylinder portion and smaller than the external shape of the second cylinder portion, and that allows the first cylinder portion to pass therethrough, and
a positioning portion that is connected with the pass portion, and that has a shape corresponding to the external shape of the second cylinder portion, the positioning portion being fitted on the second cylinder portion and supporting the second cylinder portion such that the sensor member is positioned.

2. The image forming apparatus according to claim 1, wherein the first cylinder portion and the second cylinder portion have substantially circular cylindrical shapes.

3. The image forming apparatus according to claim 2, wherein the first cylinder portion and the second cylinder portion are connected by a circular truncated cone portion that is arranged between the first cylinder portion and the second cylinder portion.

4. The image forming apparatus according to claim 1, wherein a chamfer is formed at a distal end of the second cylinder portion.

5. The image forming apparatus according to claim 1, wherein the sensor member is fixed and supported at the image forming apparatus by screwing.

6. The image forming apparatus according to claim 5, wherein a position for the screwing is arranged outside an image formation width that is a predetermined width in which an image is formed.

7. The image forming apparatus according to claim 1, further comprising:
a developing device including a developer holding member that rotates while holding a developer on a surface thereof, the developing device developing a latent image that is formed on a surface of an image holding member into a visible image,
wherein the sensor member detects a density of the developer.

8. The image forming apparatus according to claim 7, wherein the sensor member includes an irradiation portion that irradiates the developer holding member with detection light from outside of the developing device, and a light-receiving portion that receives light from the developer holding member, the sensor member detecting a density of the developer based on a detection result of the light-receiving portion.

9. The image forming apparatus according to claim 7, further comprising:
the image holding member, the latent image being formed on the surface of the image holding member,
wherein the developing device is a rotational developing device including a plurality of developing units each including a developer holding member that rotates while holding a developer on a surface thereof, and a development container that houses the developer, the rotational developing device moving the developing units around a rotation shaft.

10. The image forming apparatus according to claim 9, wherein the developing device and the sensor member are detachably attached to the image forming apparatus in a predetermined attachment/detachment direction.

11. The image forming apparatus according to claim 10, wherein the developing device is supported detachably and attachably through an inner space in a direction in which the sensor member is attached and detached, the developing device being arranged downstream of the sensor member in a direction in which the sensor member is mounted.

12. The image forming apparatus according to claim 1, wherein the second recess portion is a through hole.

13. The image forming member according to claim 1, wherein the insertion portion extends along a direction in which the sensor member is attached and detached.

14. A sensor member that is supported by an image forming apparatus, comprising:
a first supported member and a second supported member that are at opposite ends in a longitudinal direction of the sensor member, the first supported member being one of a first protruding portion and a first recess portion, the second supported member being one of a second protruding portion and a second recess portion, wherein the other one of the first protruding portion and the first recess portion is arranged on a support portion of the image forming apparatus and the other one of the second protruding portion and the second recess portion is arranged in the support portion, the second protruding portion having
a first cylinder portion that extends in a longitudinal direction of the second protruding portion, and
a second cylinder portion that is arranged at a position closer to an end of the second protruding portion than the first cylinder portion in the longitudinal direction of the second protruding portion, the second cylinder portion connected to the first cylinder portion in the longitundinal durection, having a larger external shape than an external shape of the first cylinder portion, and extending in the longitudinal direction of the second protruding portion, and the second recess portion having an insertion portion that allows the second protruding portion to be inserted, a positioning portion that is sized to position the sensor member, and engages with the second protruding portion, and a pass portion that connects the insertion portion and the positioning portion, the insertion portion being larger than the positioning portion.

15. The sensor member according to claim 14, wherein the first cylinder portion and the second cylinder portion have substantially circular cylindrical shapes.

16. An image forming apparatus, comprising:

a developing device including a developer holding member that rotates while holding a developer on a surface thereof, the developing device developing a latent image that is formed on a surface of an image holding member into a visible image; and the sensor member according to claim 15 that detects a density of the developer.

17. The sensor member according to claim 14, wherein the first cylinder portion and the second cylinder portion are connected by a circular truncated cone portion that is arranged between the first cylinder portion and the second cylinder portion.

18. The sensor member according to claim 14, wherein the second recess portion is a through hole.

* * * * *